(12) United States Patent
Miyazaki et al.

(10) Patent No.: US 7,850,839 B2
(45) Date of Patent: Dec. 14, 2010

(54) BIOSENSOR, MEASURING INSTRUMENT FOR BIOSENSOR, AND METHOD OF QUANTIFYING SUBSTRATE

(75) Inventors: Shoji Miyazaki, Matsuyama (JP);
Hiroyuki Tokunaga, Onsen-gun (JP);
Yoshinobu Tokuno, Iyo-gun (JP);
Kazuhiro Matsumoto, Matsuyama (JP);
Yasuhiko Sawada, Matsuyama (JP)

(73) Assignee: Panasonic Corporation, Osaka (JP)

( * ) Notice: Subject to any disclaimer, the term of this patent is extended or adjusted under 35 U.S.C. 154(b) by 952 days.

(21) Appl. No.: 11/378,944

(22) Filed: Mar. 16, 2006

(65) Prior Publication Data

US 2006/0175207 A1 Aug. 10, 2006

Related U.S. Application Data

(62) Division of application No. 10/182,236, filed as application No. PCT/JP01/10525 on Nov. 30, 2001, now Pat. No. 7,232,510.

(30) Foreign Application Priority Data

Nov. 30, 2000 (JP) ............................. 2000-364225
Nov. 22, 2001 (JP) ............................. 2001-357144

(51) Int. Cl.
*G01N 27/327* (2006.01)
(52) U.S. Cl. ................................. 205/777.5; 204/403.02
(58) Field of Classification Search ............ 204/403.01, 204/403.02, 406; 205/777.5, 792
See application file for complete search history.

(56) References Cited

U.S. PATENT DOCUMENTS

| 4,426,451 | A | 1/1984 | Columbus |
| 5,120,420 | A | 6/1992 | Nankai et al. |
| 5,230,866 | A | 7/1993 | Shartle et al. |

(Continued)

FOREIGN PATENT DOCUMENTS

EP 0 471 986 A 2/1992

(Continued)

OTHER PUBLICATIONS

Office action dated Jan. 21, 2010 in U.S. Appl. No. 11/378,682.*

(Continued)

*Primary Examiner*—Kaj K Olsen
(74) *Attorney, Agent, or Firm*—Amster, Rothstein & Ebenstein LLP

(57) ABSTRACT

A method of measuring a quantity of a substrate contained in sample liquid is provided. This method can reduce measurement errors caused by a biosensor. The biosensor includes at least a pair of electrodes on an insulating board and is inserted into a measuring device which includes a supporting section for supporting detachably the biosensor, plural connecting terminals to be coupled to the respective electrodes, and a driving power supply which applies a voltage to the respective electrodes via the connecting terminals. One of the electrodes of the biosensor is connected to the first and second connecting terminals of the measuring device only when the biosensor is inserted into the measuring device in a given direction, and has a structure such that the electrode becomes conductive between the first and second connecting terminals due to a voltage application by the driving power supply.

9 Claims, 22 Drawing Sheets

U.S. PATENT DOCUMENTS

| | | | |
|---|---|---|---|
| 5,264,103 A | 11/1993 | Yoshioka et al. | |
| 5,266,179 A | 11/1993 | Nankai et al. | |
| 5,288,387 A | 2/1994 | Ito et al. | |
| 5,352,351 A | 10/1994 | White et al. | |
| 5,405,511 A | 4/1995 | White et al. | |
| 5,438,271 A | 8/1995 | White et al. | |
| 5,582,697 A * | 12/1996 | Ikeda et al. | 205/777.5 |
| 5,651,869 A | 7/1997 | Yoshioka et al. | |
| 5,653,863 A | 8/1997 | Genshaw et al. | |
| 5,660,163 A | 8/1997 | Schulman et al. | |
| 5,798,031 A | 8/1998 | Charlton et al. | |
| 5,912,134 A | 6/1999 | Shartle | |
| 5,942,102 A | 8/1999 | Hodges et al. | |
| 6,004,441 A | 12/1999 | Fujiwara et al. | |
| 6,071,391 A | 6/2000 | Gotoh et al. | |
| 6,120,676 A | 9/2000 | Heller et al. | |
| 6,143,164 A | 11/2000 | Heller et al. | |
| 6,156,270 A | 12/2000 | Buechler | |
| 6,212,417 B1 | 4/2001 | Ikeda et al. | |
| 6,258,229 B1 | 7/2001 | Winarta et al. | |
| 6,287,451 B1 | 9/2001 | Winarta et al. | |
| 6,299,757 B1 | 10/2001 | Feldman et al. | |
| 6,309,526 B1 | 10/2001 | Fujiwara et al. | |
| 6,349,230 B1 | 2/2002 | Kawanaka | |
| 6,416,641 B1 | 7/2002 | Ikeda et al. | |
| 6,475,372 B1 | 11/2002 | Ohara et al. | |
| 6,576,101 B1 | 6/2003 | Heller et al. | |
| 6,576,117 B1 | 6/2003 | Iketaki et al. | |
| 6,599,406 B1 | 7/2003 | Kawanaka et al. | |
| 6,616,819 B1 | 9/2003 | Liamos et al. | |
| 6,645,359 B1 | 11/2003 | Bhullar et al. | |
| 6,814,843 B1 | 11/2004 | Bhullar et al. | |
| 6,821,410 B2 | 11/2004 | Watanabe et al. | |
| 7,018,843 B2 | 3/2006 | Heller | |
| 7,050,843 B2 | 5/2006 | Shartle et al. | |
| 7,232,510 B2 | 6/2007 | Miyazaki et al. | |
| 7,250,105 B1 | 7/2007 | Davies et al. | |
| 7,258,769 B2 | 8/2007 | Cui et al. | |
| 7,276,146 B2 | 10/2007 | Wilsey | |
| 7,276,147 B2 | 10/2007 | Wilsey | |
| 7,287,318 B2 | 10/2007 | Bhullar et al. | |
| 7,338,639 B2 | 3/2008 | Burke et al. | |
| 2002/0134676 A1 | 9/2002 | Watanabe et al. | |
| 2006/0175206 A1 | 8/2006 | Miyazaki et al. | |
| 2008/0110754 A1 | 5/2008 | Miyazaki et al. | |

FOREIGN PATENT DOCUMENTS

| | | |
|---|---|---|
| EP | 0 539 814 A2 | 10/1992 |
| EP | 0 537 761 A | 4/1993 |
| EP | 0 732 406 A1 | 9/1996 |
| EP | 0 878 713 A2 | 11/1998 |
| EP | 0 984 069 A | 3/2000 |
| EP | 1 239 048 A | 9/2002 |
| JP | 01-291153 | 11/1989 |
| JP | 03-054447 | 3/1991 |
| JP | 06 109688 A | 4/1994 |
| JP | 11344461 | 12/1994 |
| JP | 8502589 | 3/1996 |
| JP | 9189675 | 7/1997 |
| JP | 11-304748 | 11/1999 |
| JP | 11304748 A | 11/1999 |
| JP | 2000-019147 | 1/2000 |
| JP | 2000-221121 | 8/2000 |
| WO | WO 94/29704 A | 12/1994 |
| WO | WO 97/18464 A | 5/1997 |
| WO | WO 99/05516 A1 | 2/1999 |
| WO | WO 01/36953 A1 | 5/2001 |
| WO | WO 94/29706 | 12/2004 |
| WO | WO 9429705 | 12/2004 |

OTHER PUBLICATIONS

European Search Report dated Jul. 24, 2009 in connection with EP Patent Application No. 09007943.5, 6 pages.
European Search Report dated Jul. 23, 2009 in connection with EP Patent Application No. 09007942.7, 5 pages.
European Search Report dated Jul. 24, 2009 in connection with EP Patent Application No. 09007944.3, 7 pages.
Machine Translation of JP 11-304,748, published Nov. 1999, 16 pages.
"Supplemental European Search Report" dated Apr. 21, 2009 issued by the European Patent Office in connection with European Patent Application No. 01998816.1, 6 pages.

* cited by examiner (a)

(b)

(c)

(d)

(e)

(f)

(g)

Sensitivity Compensation Table

FIG. 12

| Current (mV) | F1 | F2 | F3 | F4 | F5 | F6 | F7 |
|---|---|---|---|---|---|---|---|
| 15 | 4 | 4 | 5 | 6 | 1 | 2 | 3 |
| 25 | 17 | 17 | 18 | 19 | 14 | 15 | 16 |
| 35 | 30 | 30 | 31 | 32 | 27 | 28 | 29 |
| ⋮ | ⋮ | ⋮ | ⋮ | ⋮ | ⋮ | ⋮ | ⋮ |
| 400 | 685 | 685 | 686 | 687 | 682 | 683 | 684 |
| 430 | 820 | 820 | 821 | 822 | 817 | 818 | 819 |

| | mg/dL | Coefficient (%) |
|---|---|---|
| 1 | 29 | -45.1 |
| 2 | 42 | -46.2 |
| 3 | 54 | -47.2 |
| 4 | 89 | -43.2 |
| 5 | 124 | -39.2 |
| 6 | 162 | -36.5 |
| 7 | 200 | -33.7 |
| 8 | 245 | -31.3 |
| 9 | 290 | -28.9 |
| 10 | 368 | -24.3 |
| 11 | 445 | -19.7 |
| 12 | | |
| 13 | | |

...

(b) <15°C> T15

| | mg/dL | Coefficient (%) |
|---|---|---|
| 1 | 30 | -44.0 |
| 2 | 43 | -44.9 |
| 3 | 56 | -45.8 |
| 4 | 91 | -42.1 |
| 5 | 126 | -38.4 |
| 6 | 165 | -35.6 |
| 7 | 203 | -32.8 |
| 8 | 251 | -30.2 |
| 9 | 229 | -27.6 |
| 10 | 374 | -23.6 |
| 11 | 449 | -19.5 |
| 12 | | |
| 13 | | |

(c) <20°C> T20

| | mg/dL | Coefficient (%) |
|---|---|---|
| 1 | 30 | -42.9 |
| 2 | 44 | -43.7 |
| 3 | 58 | -44.4 |
| 4 | 183 | -35.4 |
| 5 | 308 | -26.4 |
| 6 | 257 | -29.2 |
| 7 | 206 | -31.9 |
| 8 | 257 | -29.2 |
| 9 | 308 | -26.4 |
| 10 | 381 | -22.8 |
| 11 | 453 | -19.2 |
| 12 | | |
| 13 | | |

(a)

(b)

(a)

(b)

BIOSENSOR, MEASURING INSTRUMENT FOR BIOSENSOR, AND METHOD OF QUANTIFYING SUBSTRATE

CROSS-REFERENCE TO RELATED APPLICATIONS

This application is a divisional of U.S. patent application Ser. No. 10/182,236, filed Nov. 21, 2002, now U.S. Pat. No. 7,232,510, which is a 35 U.S.C. §371 U.S. National Phase of PCT Application No. PCT/JP01/10525, filed Nov. 30, 2001, and claims priority to Japanese Application No. 2000-364225, filed Nov. 30, 2000, and Japanese Application No. 2001-357144, filed Nov. 22, 2001, the contents of all of which are hereby incorporated by reference.

TECHNICAL FIELD

The present invention relates to a biosensor for measuring the quantity of a substrate included in sample liquid and a measuring device for the biosensor. Further, the present invention provides a novel measuring method which reduces measurement errors caused by a biosensor.

BACKGROUND ART

Biosensors measure the quantity of a substrate included in sample liquid. The sensors utilize molecular recognition capability of bio material such as germ, enzyme, antibody, DNA, RNA and the like, and uses the bio material as a molecular recognizing element. In other words, when the bio material recognizes an objective substrate, it reacts such that the germ breathes, emits light, consumes oxygen, or causes enzyme reaction. The biosensors utilize those reactions and measure the quantity of the substrate included in the sample liquid. Among the biosensors, enzyme sensors have been promoted to practical use. For instance, an enzyme sensor for glucose, lactic acid, cholesterol, and amino acid is used in medical measurement and food industry. The enzyme sensor reduces an electron carrier with an electron produced by the reaction between the substrate and the enzyme included in the sample liquid, i.e., specimen. A measuring device measures the reduced amount of the electron carrier electrochemically, so that quantative analysis of the specimen is carried out.

Various kinds of biosensors, such as the one discussed above, have been proposed. A conventional biosensor, biosensor Z, will be described hereinafter. FIG. 16(a) shows a perspective exploded view of biosensor Z. FIG. 16(b) shows a structure of an electrode formed at a tip of biosensor Z. A method of measuring a quantity of a substrate in a sample liquid will be described with reference to FIG. 16(b).

First, biosensor Z is inserted into a measuring device. The measuring device applies a given voltage across counter electrode 1103a and measuring electrode 1103b. Then the sample liquid is supplied to inlet 1106b of a sample supplying path. The sample liquid is sucked into the supplying path due to capillary phenomenon, and passes on counter electrode 1103a, which is nearer to inlet 1106b, and arrives at measuring electrode 1103b. Then reagent layer 1105 starts dissolving. At this time, the measuring device detects an electrical change occurring between counter electrode 1103a and measuring electrode 1103b, and starts measuring the quantity. The quantity of the substrate included in the sample liquid is thus measured.

Specifically, oxidoreductase and an electron acceptor retained in the reagent layer dissolve into the sample liquid, and enzyme reaction progresses between the substrate in the liquid. Then the electron acceptor is reduced. After the reaction finishes, the reduced electron acceptor is oxidized electrochemically. A concentration of the substrate can be measured using an oxidation current measured when the acceptor is oxidized.

However, the conventional biosensor Z has some problems to be solved. In particular, when the measuring device detects the electrical change in reagent layer 1105, various factors influence measurement accuracy and sensitivity of the measuring device.

First, an incorrect operation by a user influences them. For instance: (1) After the user supplies the sample liquid to the sample supplying path, the user adds another sample liquid before the measuring device completes the measurement; (2) The user tries to measure the quantity with a biosensor which have been already used; (3) The user supplies the sample liquid to a incorrect place; (4) The user inserts the biosensor into the measuring device in a wrong direction; and (5) When supplying the sample liquid, the user fails to pinpoint an inlet of the sample supplying path, has the sample liquid attach to a surrounding area, and thus has the sample liquid not run into the path. Thus some ways have been desired to avoid those incorrect operations which influence the measurement accuracy. In particular, preventing aged users from the incorrect operations is required.

Second, characteristics of an object to be measured influence them. For instance, when a glucose concentration of human blood is measured with a biosensor, a viscosity of the blood may influence measurement accuracy. Hematocrit, which is generally known as an index of blood viscosity, indicates a volume percentage of erythrocyte included in the blood. Blood in a person who does not suffer from anemia includes 50-60 volume % of water and 40-50 volume % of erythrocyte. If suffering from renal anemia due to chronic renal failure, a person has blood have the volume percentage of hematocrit decrease to less than 15%. Appropriate treatment requires to restrain the influence to hematocrit in the blood for accurate measurement of glucose concentration in the blood of, e.g., a diabetic.

Third, a temperature around the measuring device influences them. Measuring devices available in the market for biosensors have been downsized so that users can carry it with them. Soon after moving into indoors from the outside, a user may try to measure the quantity. In this case, the measurement may start before a temperature in the measuring device becomes stable. A sharp change in temperature influences the oxidation current corresponding to a substrate concentration, and thus may lower the measurement accuracy. A body temperature of the user, upon being transmitted to the measuring device via, e.g., the user's hand, might influence the measurement accuracy.

The present invention thus aims to provide a biosensor being handled easily and having excellent measurement accuracy, a method of measuring quantity using the biosensor, and a measuring device using the biosensor.

SUMMARY OF THE INVENTION

For solving the above problems, a first aspect of the present invention provides a biosensor for measuring the quantity of a substrate included in sample liquid. The biosensor is inserted to a measuring device which includes a supporting section for supporting detachably a biosensor which is formed of at least a pair of electrodes on an insulating board, plural connecting terminals electrically connected to the electrodes respectively, and a driving power supply for applying a voltage to the electrodes via the connecting terminals. One of the electrodes of the biosensor is connected to first and second connecting terminals of the measuring device only when the biosensor is inserted into the supporting section of the measuring device in a given direction. Then, the one of the electrodes becomes conductive due to a voltage application by the driving power supply. The electrodes have such a structure discussed above.

A conductive layer may be formed on at least a part of the insulating board, and the conductive layer is divided by slits, thereby forming a counter electrode and a measuring electrode, and upon request, a detecting electrode may be also formed.

A second aspect of the present invention aims to provide a measuring device to be used with a biosensor, and to measures a quantity of a substrate included in sample liquid. The measuring device includes a supporting section for supporting detachably the biosensor including at least a pair of electrodes on an insulating board, plural connecting terminals electrically connected to the electrodes, respectively, and a driving power supply for applying a voltage to the electrodes via the connecting terminals. The measuring device includes first and second connecting terminals can be connected to either one of electrodes of the biosensor only when the biosensor is inserted into the supporting section in a given direction. Thus conductivity can be detected between the first and the second connecting terminals by applying a voltage from the driving power supply to the first and second terminals, respectively.

It is also possible that the measuring device may determine that the biosensor is not inserted in the given direction if the conductivity is not detected. It is also possible that the measuring device may include an output section which outputs the determination to outside when the device determines that the biosensor is not inserted in the given direction.

A third aspect of the present invention provides a method of measuring a quantity of a substrate included in sample liquid with a biosensor. The biosensor includes an electrode section including: a counter electrode, a measuring electrode, and a detecting electrode on at least a part of an insulating board; a sample supplying path for supplying the sample liquid to the electrode section; and a reagent layer for reacting on the sample liquid supplied via the sample supplying path. The biosensor is inserted into a measuring device which includes a supporting section for supporting detachably the biosensor, connecting terminals, and a driving power supply for applying a voltage to the electrode section. When the biosensor is inserted into the supporting section of the measuring device, the driving power supply applies a voltage to a first electrode group and a second electrode group. The first group is formed of the counter electrode and the measuring electrode, and the second group is formed of the detecting electrode and one of the counter electrode and the measuring electrode.

In the biosensor, the detecting electrode among the counter electrode, the measuring electrode, and the detecting electrode is disposed most downstream along the sample supplying path, i.e., from a sample inlet along the sample flowing direction. It may be determined whether or not the sample liquid is supplied sufficiently for the measurement depending on whether or not respective electric currents from the first and second electrode groups exceed respective given thresholds.

After the electric current from the first electrode group exceeds the given threshold, if the current from the second group does not exceed the given threshold within a predetermined period, it may be determined that the sample liquid is insufficient. In this case, the measuring device may output the determination to the outside.

After the electric current from the first electrode group exceeds the given threshold, if the current from the second group does not exceed the given threshold within the predetermined period, an operator may hold a measuring step in order to add the sample liquid.

In the sample supplying path of the biosensor, the detecting electrode among the counter electrode, the measuring electrode, and the detecting electrode is disposed most downstream along the sample flowing direction from the sample inlet. An air hole for accelerating the flowing of the sample liquid is formed downstream against the detecting electrode. If the electric current from the second electrode group exceeds the predetermined threshold before the first group, and if the current from the first group does not exceed the threshold within a given period, it may be determined that the sample liquid is sucked from the air hole by mistake.

A measured quantity of the substrate corresponding to electric current detected by the electrode section may be compensated according to a lapse of time since the current from the first electrode group exceeds the threshold until the current from the second electrode group exceeds the threshold.

The measuring device may include a memory storing measured data which shows correspondence between a quantity of the substrate included in the sample liquid and a current detected by the biosensor. The measuring device refers to the measured data, thereby determining the quantity of the substrate corresponding to the detected current.

After the sample liquid is supplied to the sample supplying path, reaction between the sample liquid and the reagent layer is incubated during a certain time, and the quantity of the substrate is then measured. In this case, the incubating time may vary according to a lapse of time since the current from the first electrode group exceeds the threshold until the current from the second group exceeds the threshold. The driving power supply may apply a voltage to the first group and the second group alternately at constant intervals.

A fourth aspect of the present invention aims to provide a method of measuring a quantity of a substrate. This method uses a biosensor including a reagent layer which reacts specifically on the substrate in sample liquid. The method also uses a measuring device for measuring the quantity of the substrate included in the sample liquid from a sample produced by the reaction between the sample liquid and the reagent layer. The measuring device includes a temperature measuring section for measuring a temperature in the reaction progress between the sample liquid and the reagent layer and a temperature compensation memory for storing plural compensation tables of measured data. The compensation tables are prepared for each temperature range. The measuring device selects a compensation table according to a temperature measured by the temperature measuring section, and calculates a compensation value responsive to a measured quantity of the substrate for compensation.

The biosensor may include an electrode section including a counter electrode and a measuring electrode which are disposed on at least a part of an insulating board. The measuring device may apply a voltage to the electrode section and detect an electric current from the electrodes.

A fifth aspect of the present invention aims to provide a method of measuring, with a measuring device, a quantity of a substrate included in sample liquid supplied to a biosensor. The measuring device includes a temperature measuring section for measuring a temperature inside the measuring device. The temperature measuring section detects a temperature change between a temperature measured before the measurement of the substrate quantity and a temperature at the measurement. According to the temperature change, the measuring device determines whether the substrate quantity is to be measured or not.

If the temperature change exceeds a given threshold, the measurement may be cancelled. A temperature prior to the measurement may be measured intermittently.

A sixth aspect of the present invention aims to provide a method of measuring a quantity of a substrate included in sample liquid with a biosensor and a measuring device. The biosensor includes an electrode section including a counter electrode, a measuring electrode, and a reagent layer for reacting on sample liquid supplied to the electrode section which are disposed on at least part of an insulating board. The measuring device includes a supporting section for detachably supporting the biosensor, connecting terminals, and a driving power supply for applying a voltage to the electrode section. The driving power supply applies a voltage to the electrode section, and an electric current from the electrode section is detected, thereby measuring the quantity of the substrate included in the sample liquid. The measuring device applies a first voltage during a first period to the electrode section of the biosensor supported by the supporting section. After this voltage application during the first period, the voltage application is halted during a standby period. After the standby period, a second voltage is applied to the electrode section during a second period, and the current from the electrode section is measured, thereby measuring the quantity of the substrate. The first voltage is greater than the second voltage.

A seventh aspect of the present invention aims to provide a biosensor including two boards which are bonded to each other for forming a sample supplying path for taking sample liquid between the boards. The sample liquid is poured into an opening at respective ends of the boards as an inlet. The respective ends of the boards are located at different places from each other in a plan view of the biosensor.

BRIEF DESCRIPTION OF THE DRAWINGS

FIG. 12 shows data CA of a calibration curve.

FIG. 13 shows temperature compensation tables.

DETAILED DESCRIPTION OF EXEMPLARY EMBODIMENTS

Exemplary embodiments of the present invention will be described hereinafter with reference to the accompanying drawings. The embodiments discussed here are only examples, and the present invention is not necessarily limited to these embodiments.

Exemplary Embodiment 1

Figure 1:
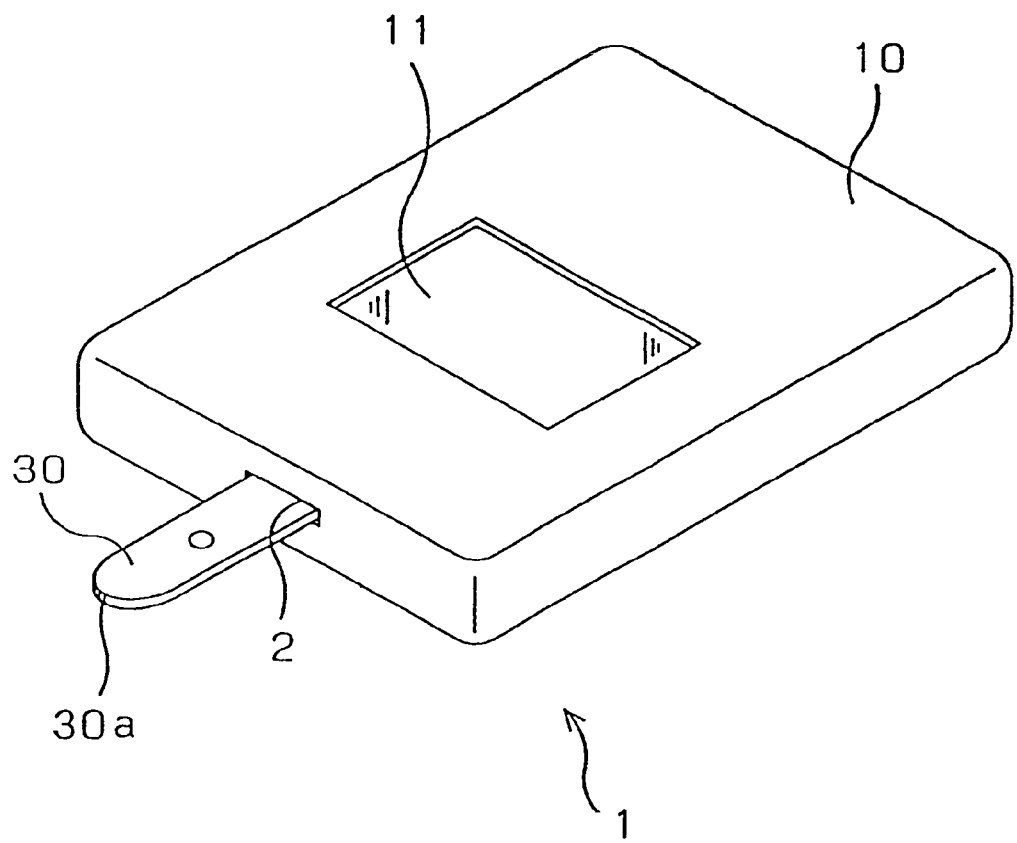
FIG. 1 shows a biosensor system in accordance with a first exemplary embodiment of the present invention.

The first embodiment will be demonstrated hereinafter with reference to the accompanying drawings. FIG. 1 shows a biosensor system in accordance with the first embodiment of the present invention. Biosensor system 1 includes biosensor 30 and measuring device 10 having biosensor 30 mounted detachably thereto. Sample liquid is dripped on sample-drip point 30a located at a tip of biosensor 30. A quantity of a substrate included in the dripped sample liquid is measured by measuring device 10.

Measuring device 10 includes, for instance, supporting section 2 to which biosensor 30 is detachably mounted and display 11 which shows a measured quantity of the substrate included in the sample liquid dripped on sample-drip point 30a.

To measure a quantity of a substrate included in sample liquid with biosensor system 1, first, a user inserts biosensor 30 into measuring device 10. Then the user drips the sample liquid on sample-drip point 30a while measuring device 10 applies a certain voltage to electrodes of biosensor 30. The sample liquid dripped, upon being sucked into biosensor 30, make a reagent layer start dissolving. Measuring device 10 detects an electrical change generated between the electrodes of biosensor 30, then starts measuring the quantity of the substrate.

Biosensor system 1 in accordance with the first embodiment is suitable to processing human blood as a sample liquid among others, and measuring a quantity of glucose, lactic acid, cholesterol included in the human blood as a substrate. Measuring the quantity of the substrate included in human body fluid is very important for diagnosis and medical treatment for a specific physiological abnormality. In particular, a diabetic is required to monitor his glucose concentration in the blood frequently.

The following demonstration refers to measuring a quantity of glucose included in human blood. However, biosensor system 1 in accordance with the first embodiment can measure a quantity of lactic acid, cholesterol and other substrates by selecting an appropriate enzyme as well.

Next, components forming biosensor 30 will be described with reference to FIG. 2, an exploded perspective view of biosensor 30. Insulating board 31 (hereinafter called simply "board") is made of, e.g., polyethylene terephthalate. On a surface of board 31, a conductive layer, which is made of a noble metal such as gold and palladium, or an electrically conductive substance such as carbon, is formed by screen printing or sputtering evaporation. The conductive layer may be formed on the entire or at least a part of the surface. Reference numeral 32 denotes an insulating board having air hole 33 formed at its center. Spacer 34 having a notch is disposed between boards 31 and 32, so that board 32 is integrated to board 31.

On board 31, the conductive layer is divided by a plurality of slits into counter electrode 37, measuring electrode 38, and detecting electrode 39. In detail, the conductive layer is divided by the following slits: substantially arc-shaped slit 40 formed on counter electrode 37; slits 41a and 41c formed vertically to a side of board 31; slits, 41b, 41d, and 41f and V-shaped slit 41e. The slits form counter electrode 37, measuring electrode 38 and detecting electrode 39. Each electrode may can be formed on at least a part of board 31. Measuring device 10 may connected to the electrodes with lead wires.

Spacer 34 is placed for covering counter electrode 37, measuring electrode 38, and detecting electrode 39 on board 31. The notch shaped in a rectangular provided at a center in a front section of spacer 34 forms sample supplying path 35. The sample liquid is dripped to inlet 30a of sample supplying path 35. The sample liquid dripped to inlet 30a is sucked by capillary phenomenon in an approximately horizontal direction (along arrow AR in FIG. 2) toward air hole 33.

Reference numeral 36 denotes a reagent layer formed by applying reagent, which contains enzymes, electron acceptors, amino acid, sugar alcohol and the like, to portions of counter electrode 37, measuring electrode 38 and detecting electrode 39, the portions which are exposed from the notch of spacer 34.

The enzymes may employ the following materials: glucose oxidase, lactate oxidase, cholesterol oxidase, cholesterol estrase, uricase, ascorbate acid oxidase, bilirubin oxidase, glucose dehydrogenase, lactate dehydrogenase.

The electron acceptor preferably employs ferricyanide kalium, however, may employ p-benzoquinone and its derivatives, phenacine methor sulphate, methylene blue, and pherocane and its derivatives.

In the biosensor system in accordance with the first embodiment, glucose oxidase is used as oxidoreductase retained in reagent layer 36, and ferricyanide kalium is used as the electron acceptor in order to measure the glucose concentration in human blood.

The oxidoreductase and the electron acceptor dissolve in the sample liquid (human blood in this embodiment) which is sucked into the sample supplying path, and then the glucose, a substrate in the sample liquid, reacts with the oxidoreductase and the electron acceptor, and the enzyme reaction progresses. Then the electron acceptor is reduced, thus producing ferrocyanide (ferricyanide kalium in this embodiment). After the reaction, the reduced electron acceptor, upon being oxidized electrochemically, generates a current from which the glucose concentration is measured. This series of reactions progress mainly in an area covering slits 40, 41e and detecting electrode 39. The current produced by the electrochemical change is read out through measuring electrode 38 and detecting electrode 39.

Reference numeral 42 denotes a recognizing section for recognizing, with measuring device 10, a type of biosensor 30 and a difference in output characteristics among production lots. Slits 41g and 41h are combined to portions of counter electrode 37 and detecting electrode 39 corresponding to recognizing section 42. The slits enables measuring device 10 to recognize the differences in output characteristics electrically.

Figure 3:
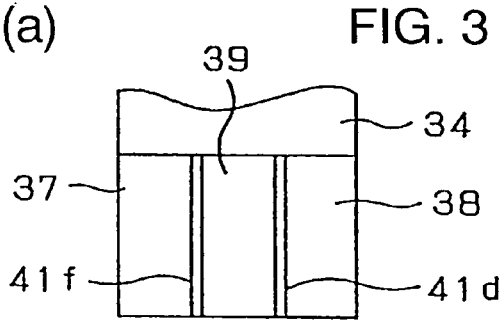
FIG. 3 shows combinations of recognizing sections of the biosensor depending on the presence of slits in accordance with the first embodiment.
Figure 3:
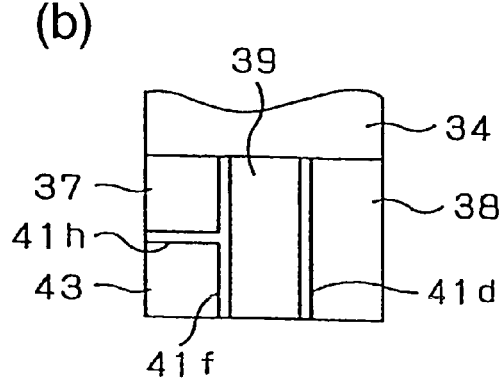
Figure 3:
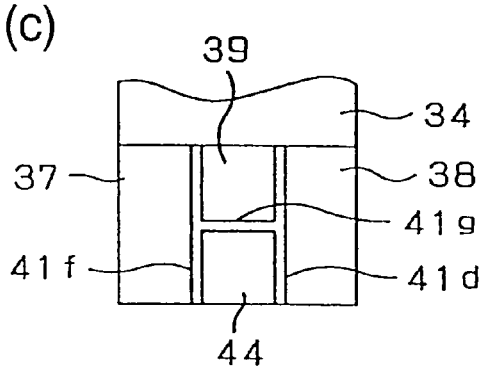
Figure 3:
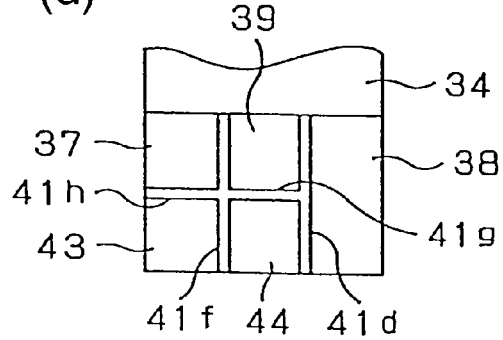
Figure 3:
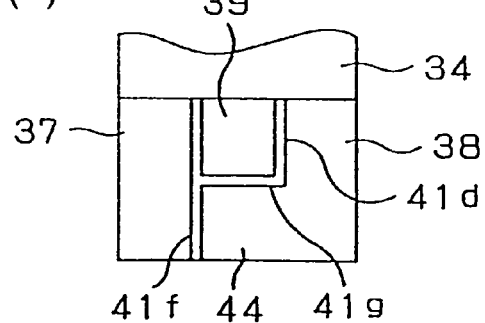
Figure 3:
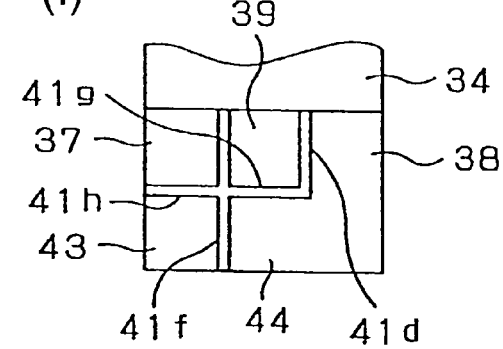
Figure 3:
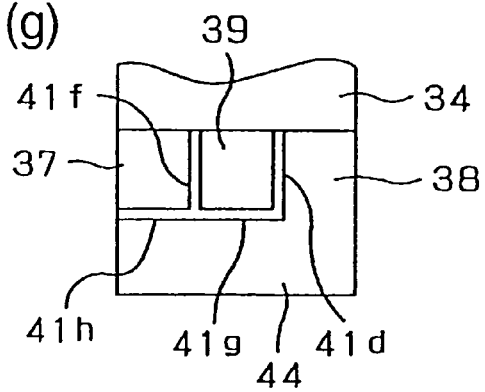

FIG. 3 shows combinations of slits depending on the presence of slits 41g, 41h in recognizing section 42 of biosensor 30. FIG. 3 illustrates seven types of combinations. For instance, FIG. 3(a) shows recognizing section 42 of biosensor 30 for measuring cholesterol. In this case, slits 41g and 41h are not formed.

FIGS. 3(b), 3(c), and 3(d) illustrate recognizing section 42 of biosensor 30 for measuring lactic acid. In FIG. 3(b), slit 41h is provided only in counter electrode 37, thereby forming compensating section 43. In FIG. 3(c), slit 41g is provided only to detecting electrode 39, thereby forming compensating section 44. In FIG. 3(d), slits 41h and 41g are provided to counter electrode 37 and detecting electrode 39, respectively, thereby forming compensating section 43 and 44, respectively. Further, FIGS. 3(e), 3(f), and 3(g) illustrate recognizing section 42 of biosensor 30 for measuring glucose. In FIG. 3(e), slit 41g is provided only to detecting electrode 39, and slit 41d is formed up to slit 41g. And thus compensating section 44 is integrally formed with measuring electrode 38. In FIG. 3(f), slit 41h is added to the section in FIG. 3(e), thereby forming compensating section 43. In FIG. 3(g), slit 41f is formed up to slit 41h shown in FIG. 3(f). Thus, correcting sections 43 and 44 are integrally formed with measuring electrode 38.

As such, a conductive area between the electrodes can be varied depending on patterns of the slits in recognizing section 42. This enables measuring device 10 to recognize the differences in output characteristics (concentrations of glucose, cholesterol, lactic acid) of biosensor 30 and errors depending on production lots. Data and a control program, since being changed appropriately to the substrate according to the recognition, enables the device to be expected in exact measurement. This allows a user not to input compensating data using a compensating chip, and prevents the user from incorrectly handling the device. This embodiment discloses the biosensor having three electrodes. However, a number of electrodes may change, and a biosensor may have at least a pair of electrodes. The patterns of the slits other than those shown in FIG. 3 may be formed.

Figure 4:
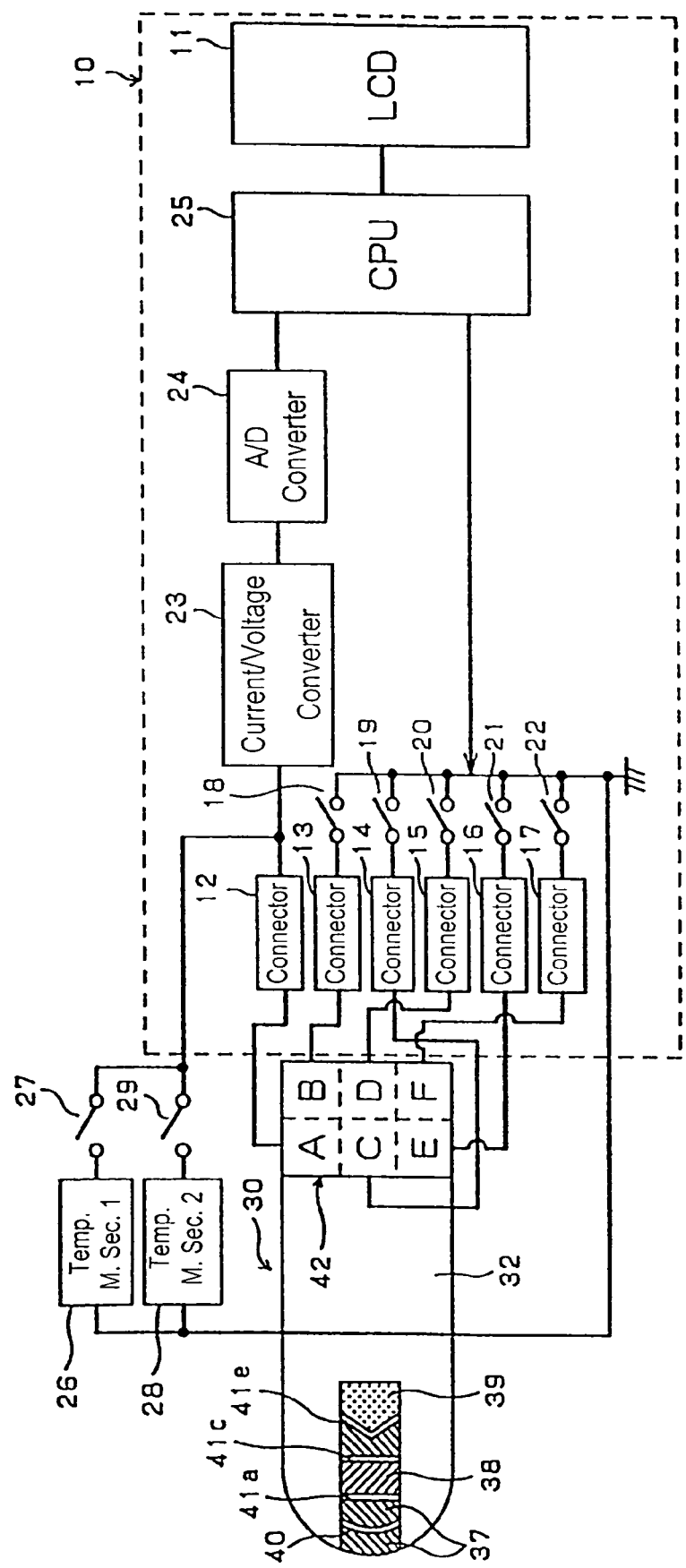
FIG. 4 shows structures of the biosensor and a measuring device in accordance with the first embodiment.

Next, a structure of measuring device 10 will be explained in detail. FIG. 4 shows structures of biosensor 30 (top view) and measuring device 10. In biosensor 30, counter electrode 37, measuring electrode 38 and detecting electrode 39 are arranged along a flowing direction of a sample from sample-drip point 30a where detecting electrode 39 is placed most downstream. Counter electrode 37 may be exchanged between measuring electrode 38 in the arrangement order. Measuring electrode 38 and detecting electrode 39 are spaced at a given distance by slits 41c and 41e. Thus, the device can determine, from an electric current changing according to an electrical change of the substrate, whether enough quantity of the sample liquid is sucked securely or not.

In measuring device 10, reference numerals 12, 13, 14, 15, 16 and 17 denote connectors connected to areas A, B, C, D, E and F, respectively, which are produced by dividing recognizing section 42 of biosensor 30 into six areas. The six areas are grouped such that the groups correspond to slits 41d, 41f and slits 41g, 41h. Area A corresponds to measuring electrode 38, area C corresponds to detecting electrode 39, and area E corresponds to measuring electrode 38. Area A is integrally formed with area B, and areas D and F correspond to compensating sections 43 and 44 shown in FIG. 3, respectively. Switches 18, 19, 20, 21 and 22 are provided between respective connectors 13, 14, 15, 16, 17 and a grounding (meaning a constant voltage, not necessarily "0"V. This definition is applicable to this description hereinafter.) Voltage to be applied to respective electrodes can be controlled at the grounding. Connectors 13, 14, 15, 16 and 17 are connected in parallel to the grounding. Switches 18 to 22, upon being turned on and off under control, select a necessary connector out of connectors 13 to 17 which is used for the measurement.

Reference numeral 23 denotes a current/voltage converter connected to connector 12, for converting a current flowing between measuring electrode 38 and other electrodes into a voltage. Reference numeral 24 denotes an A/D converter connected to current/voltage converter 23, for converting a voltage supplied from circuit 23 into a pulse. Reference numeral 25 denotes a CPU for controlling to turn on and off the switches and calculating a content of the substrate included in the sample liquid based on the pulse supplied from A/D converter 24. Reference numeral 11 denotes an LCD for displaying measured data calculated by CPU 25. Reference numerals 26 and 28 denote temperature measuring sections for measuring temperatures inside measuring device 10. Temperature measuring sections 26 and 28 are connected in parallel to each other between connector 12 and current/voltage converter 23.

In measuring device 10 in accordance with the first embodiment, voltages (mV) converted from the currents flowing between the electrodes of biosensor 30 are used for detecting changes of the currents. In other words, the voltages indicate the currents flowing between the electrodes.

Figure 5:
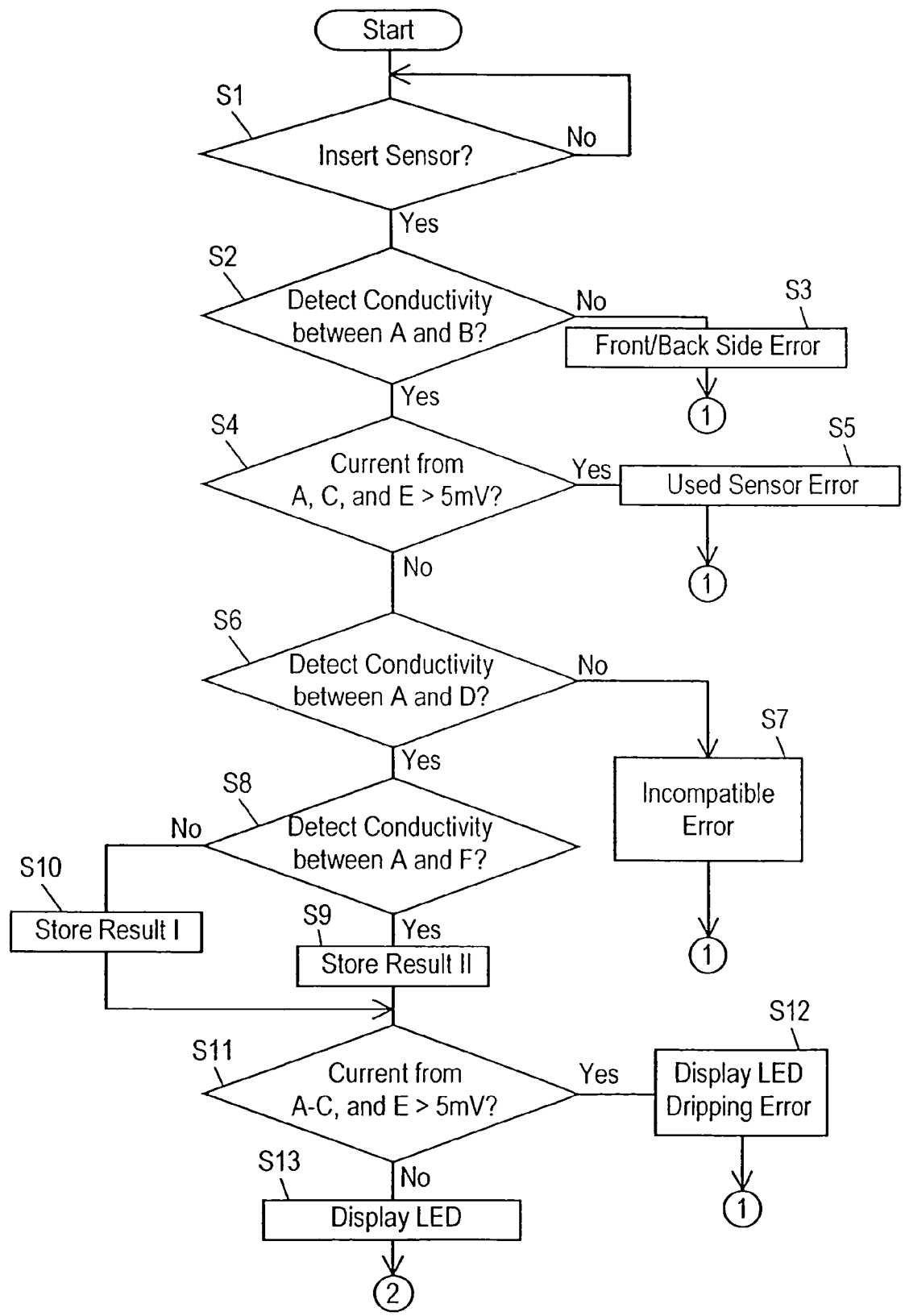
FIG. 5 is a flowchart illustrating processes of measuring a quantity of a substrate included in sample liquid by the biosensor and the measuring device.
Figure 6:
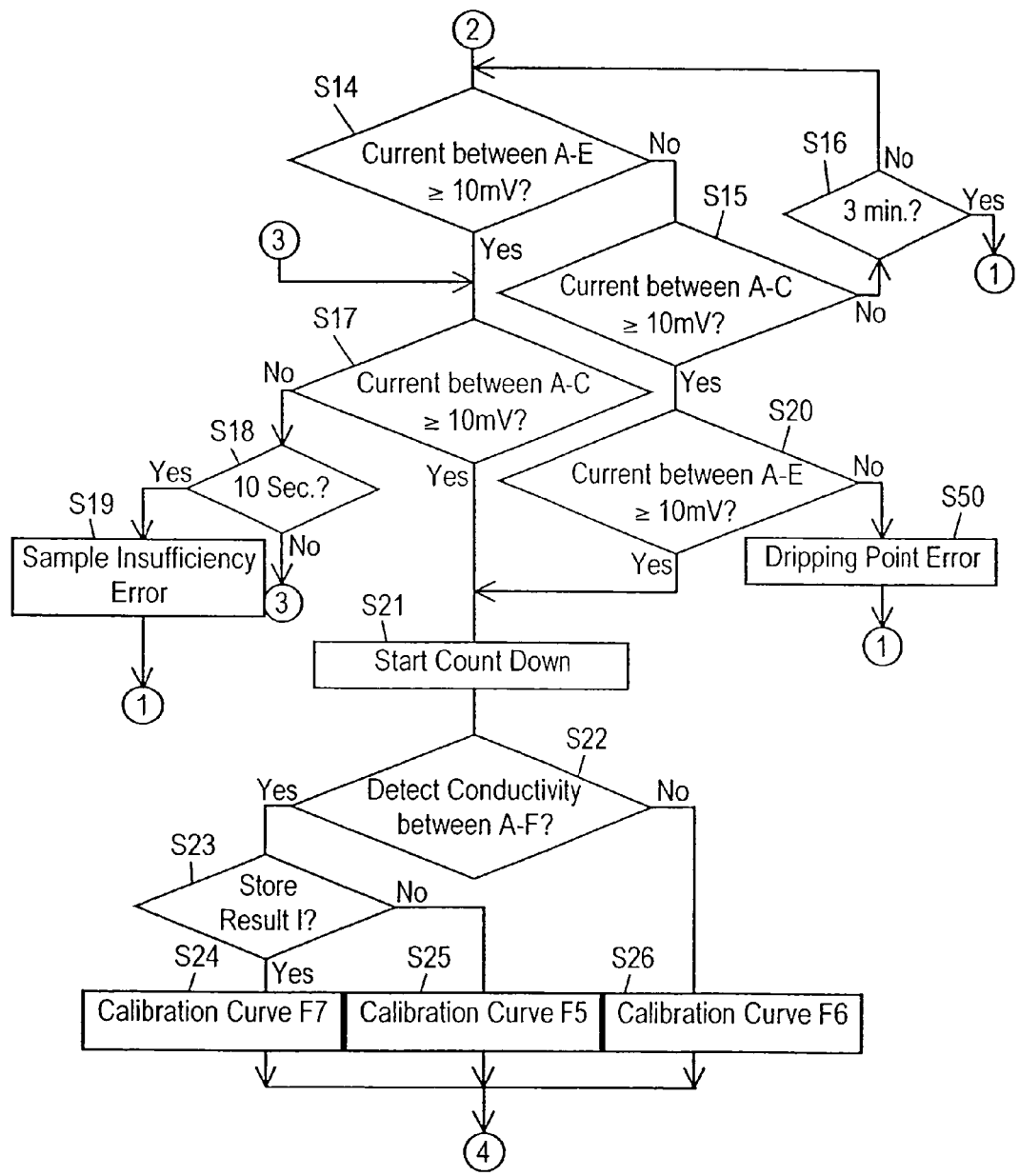
FIG. 6 is a flowchart illustrating processes of measuring a quantity of a substrate included in sample liquid by the biosensor and the measuring device.
Figure 7:
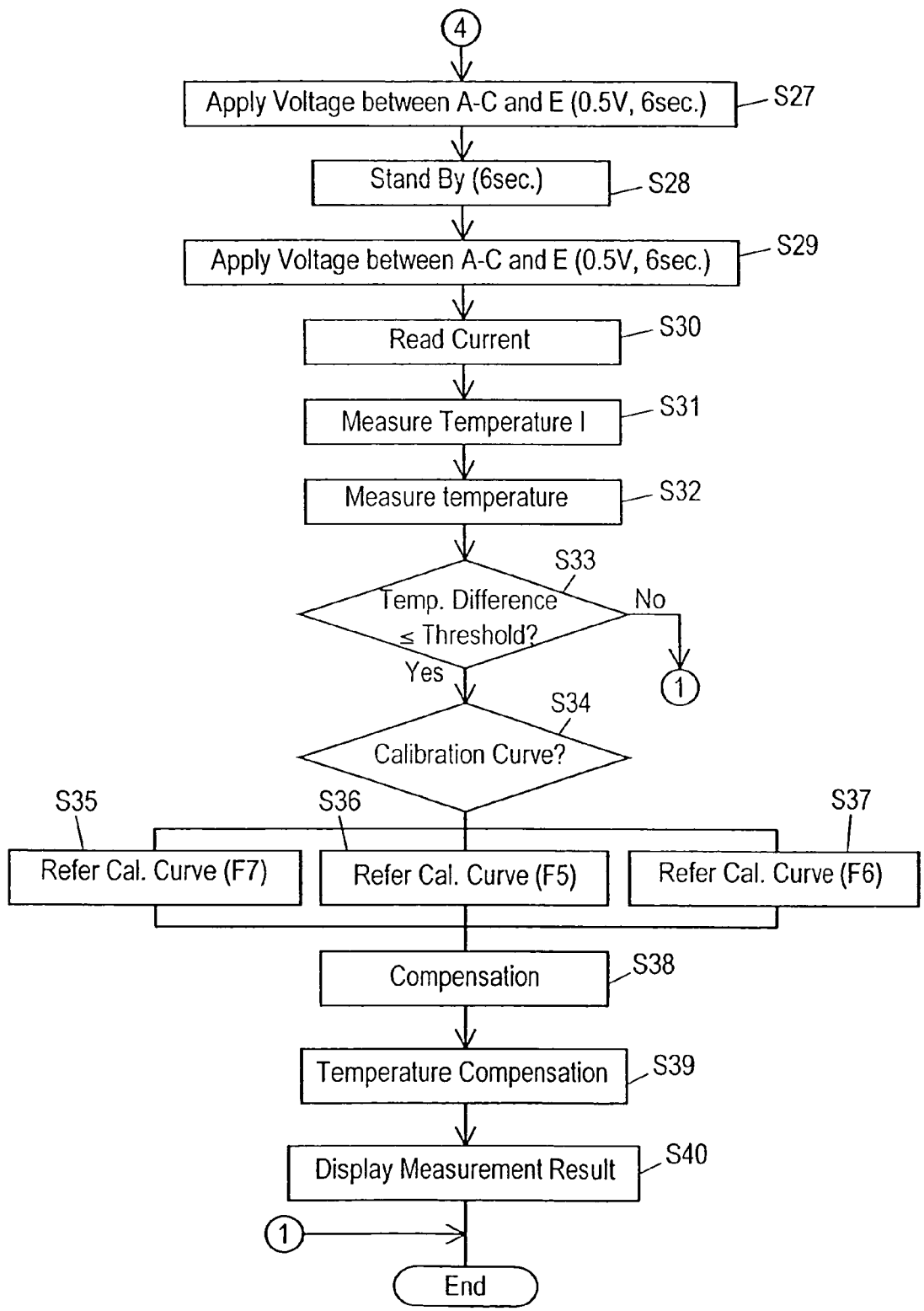
FIG. 7 is a flowchart illustrating steps of measuring a quantity of a substrate included in sample liquid by the biosensor and the measuring device.

An operations of biosensor 30 and measuring device 10 will be demonstrated with reference to FIG. 5 through FIG. 7, for measuring a content of a substrate in sample liquid by a method with biosensor 30 according to this embodiment.

First, it is determined whether or not biosensor 30 is properly inserted into supporting section 2 of measuring device 10 (Step S1). Specifically, this is determined with a switch (not shown) in a connector shown in FIG. 4. If biosensor 30 is properly inserted (step S1: Yes), conductivity between areas A and B is tested (step S2). As shown in FIG. 3, measuring electrode 38 has no slit formed therein for insulating one electrode itself such as slits 41h and 41g. In measuring electrode 38, areas A and B are connected to connectors 12 and 13, respectively. Areas A and B thus become conductive to each other without failure when biosensor 30 is inserted into measuring device 10 in a direction (a predetermined direction) such that a conductive layer of biosensor 30 is oriented normally.

Therefore, conductivity between areas A and B is tested by turning on switch 18, so that the front and back sides of biosensor 30 can be determined. If the conductivity between areas A and B is not detected (step S2: No), it is determined that biosensor 30 is inserted front-side back (reversely). Then the measuring process terminates due to an error of detecting the front and back sides (step S3). The error, when being detected, is preferably displayed on display 11, or noticed as an alarm sound from a speaker. These preparations prevent the user easily from dripping blood to biosensor 30 by mistake while biosensor 30 is inserted front-side back.

When the conductivity between areas A and B is detected (step S2: Yes), it is determined whether or not voltages detected between area A and area C and between area A and area E are greater than 5 mV (step S4). Switches 19 and 21 are simultaneously turned on, thereby allowing areas C and E to be considered to be electrically unified. Then a voltage is detected between area A and area C or E for determining whether biosensor 30 inserted in step 1 is an used one or not. This is determined since a reaction between reagent layer 36 and glucose in the blood has progressed to probably enlarge the detected voltage if biosensor 30 is the used one.

If it is determined that the voltage detected between area A and areas C is greater than 5 mV (step S4, Yes), it is recognized that biosensor 30 which is used is inserted, and the measuring process terminates due to an error of an used sensor (step S5). If being detected, the error of used sensor is preferably displayed on display 11, or noticed to a user as an alarm sound from a speaker. This prevents the user easily from dripping blood to biosensor 30 by mistake while used biosensor 30 is inserted. Next, when the voltage detected between area A and areas C, E is not greater than 5 mV (step S4: No), the patterns of the slits is recognized by recognizing section 42 of biosensor 30 which is detected to be inserted at step S1. According to the recognizing result, CPU 25 changes data and a program into appropriate ones for output characteristics of the sensor (steps S6 to S10). In the first embodiment, three patterns of the slits are available, as shown in FIGS. 3(e), 3(f), and 3(g), for a blood-sugar-level sensor which measures a glucose concentration. Specifically, first, conductivity between areas A and D is tested (step S6). Switch 20 is turned on, and then the conductivity between areas A and D is tested, so that it may be determined whether or not biosensor 30 is proper to measure a blood sugar level and not proper to measure a quantity of lactic acid or cholesterol.

If the conductivity between areas A and D is not detected (step S6: No), it is determined that biosensor 30 is incompatible with the blood-sugar-level sensor. Then the measuring process terminates (step S7), and display 11 shows an error message, or a speaker sounds an alarm for the user. These prevent the user from recognizing a measurement as a glucose concentration by mistake.

If the conductivity between areas A and D is detected (step S6: Yes), the conductivity between areas A and F is tested (step 8). Switch 22 is turned on. Then the conductivity between areas A and F is tested, so that the device can recognize differences in output characteristics due to production lots of biosensors 30 proper to blood-sugar-level sensors. CPU 25 automatically changes data and programs to which output characteristics corresponding to production lots have been reflected. Thus the user does not need a compensating chip. As a result, the biosensor and the measuring device can be handled more easily, and a higher accuracy of measurement can be expected.

If conductivity between areas A and F is detected (step S8: Yes), biosensor 30 is defined as a type shown in FIG. 3(g), and result I is stored in a memory (not shown) (step S9). If the conductivity between areas A and F is not detected (step S8: No), biosensor 30 is defined as a type shown in FIG. 3(e) or FIG. 3(f), and result II is stored in the memory (not shown) (step S10).

After the type of biosensor 30 is recognized, it is determined again whether the voltage detected between area A and areas C, E is greater than 5 mV or not (step S11). Switches 19, 21 are simultaneously turned on for detecting a current between area A and areas C, E. Then it is determined whether or not a user drips the sample liquid on biosensor 30 before measuring device 10 is ready for measurement. This process not only prevents positively the user from using used biosensor 30, but also detects that the sample liquid has been dripped by the user before the measurement is available.

If the voltage detected between area A and areas C, E is greater than 5 mV (step S11: Yes), it is determined, as a drip error, that the sample liquid is dripped before the measurement is prepared. When being detected, the drip error is preferably displayed on display 11, notified to a user with an alarm sound from a speaker, or displayed with LEDs (not shown) to give the user an alarm. The user can positively avoid a failure in operation by these operations, and a high accuracy of measurement can be expected.

If the voltage detected between area A and areas C, E is not greater than 5 mV (step S11: No), it is determined that the sample liquid is not dripped before the measurement is prepared. Then a completion of the preparation is notified to the user with LEDs (step S13). When being detected, the error is preferably displayed on display 11, notified to the user with an alarm sound from a speaker, or displayed with LEDs. Receiving this notice, the user takes blood as sample liquid from his body by himself and drips it to sample-drip point 30$a$ of biosensor 30 inserted to measuring device 10.

Next, it is determined whether or not enough quantity of the sample liquid is sucked through the sample supplying path from point 30$a$ (steps S14 to S20). In biosensor 30, counter electrode 37, measuring electrode 38, and detecting electrode 39 are arranged along sample supplying path 35 from sample-drip point 30$a$ toward a downstream of the sample liquid flow. Detecting electrode 39 is placed most downstream. Either one of a group consisting of counter electrode 37 and measuring electrode 38, or another group consisting of measuring electrode 38 and detecting electrode 39 is selected at a given interval. A voltage is applied to a selected group, so that it is determined whether or not the sample liquid is supplied in a quantity enough for measurement. In a conventional manner, a current change only between measuring electrode 38 and detecting electrode 39 is recognized. In the conventional manner, it is very difficult to identify a cause why the measurement does not start even though enough quantity of the sample liquid is supplied to the sample supplying path, or since the quantity is less than enough quantity for starting the measurement.

Specifically, for the group of counter electrode 37 and measuring electrode 38, switch 19 is turned off, and switch 21 is turned on for generating a voltage between areas A and E. For the group of measuring electrode 38 and detecting electrode 39, switch 19 is turned on, and switch 21 is turned off for generating a voltage between areas A and C. As such, switches 19 and 21 are on-off controlled, thereby selecting and switching either one of the groups easily. For easy description, hereinafter, generating the voltage between counter electrode 37 and measuring electrode 38 is referred to as generating a voltage between areas A and E. Also generating a voltage between measuring electrode 38 and detecting electrode 39 is referred to as generating a voltage between areas A and C.

Further in this embodiment, as an example, a pair of areas A and E and a pair of areas A and C are switched every 0.2 seconds, and 0.2V is applied to each pair. It is determined whether or not respective voltages measured between areas A and E and between areas A and C reaches 10 mV (a given threshold). These numbers may be changed responsive to a type of biosensors.

Back to the flowchart shown in FIG. 6, the operations of the biosensor and the measuring device will be further described hereinafter. First, a voltage of 0.2V is produced between areas A and E which are located at the upstream portion of the sample supplying path, and it is determined whether or not the voltage measured between areas A and E exceeds 10 mV (step S14). If the voltage measured does not exceed 10 mV (step S14: No), a voltage of 0.2V is applied between areas A and C located downstream of the path. Then it is determined whether the voltage measured between areas A and C exceeds 10 mV or not (step S15).

If the voltage measured between areas A and C does not exceed 10 mV (step S15: No), it is determined whether or not 3 minutes have passed since the voltage was produced between areas A and E in step S14 (step S16). If the 3 minutes has not passed (step S16: No), the processes from step S14 and onward are repeated. If respective voltages between areas A and E and between areas A and C do not reach 10 mV for 3 minutes (step S16: Yes), the measuring process terminates.

If the voltage between areas A and E is determined to reach 10 mV (step S14: Yes), it is determined whether or not the voltage between areas A and C reaches 10 mV (step S17). If the voltage between areas A and C does not reach 10 mV (step S17: No), it is determined whether or not 10 seconds (a given period) have passed since the voltage between areas A and E was determined to reach 10 mV (step S18). If the 10 seconds has not passed, the processes in steps S17 and S18 are repeated. While the 10 seconds passes, the measuring process temporarily halts until the voltage measured between areas A and C reaches 10 mV (step S18; No). In this case, the sample liquid dripped is probably insufficient, it is preferable to display the error message on display 11, or sound an alarm to a user from a speaker so that the user may understand that the sample liquid should be added. If the voltage measured between areas A and C does not reach 10 mV even after 10 seconds has passed (step S18: Yes), the measuring process terminates due to an error of specimen insufficient (step S19).

While the 10 second passes since the voltage between areas A and E was determined to reach 10 mV in step S14, if a user adds the sample liquid, a final measurement accuracy is lowered. This was found by inventors. Specifically, while the user adds the sample liquid, the substrate in the sample liquid originally dripped has reacted on the enzyme included in reagent layer 36 and enzyme reaction has progressed. Thus a reduced substance has been produced before the measurement starts. After the added sample liquid reaches between areas A and C, the quantity of the substrate is possibly measured. In this case, the reduced substance already produced influences this measurement, i.e., makes the voltage apparently greater. In other words, as a time since the voltage between areas A and E is determined to reach 10 mV in step S14 becomes longer, the measurement is influenced more by the reduced form.

In order to eliminate a measurement error caused by adding the sample liquid, a quantity of the substrate is compensated responsive to a measured voltage in measuring device 10 in accordance with this embodiment. The compensation depends on the lapse of time (delay time) since the voltage between areas A and E was determined to reach 10 mV in step S14 until the voltage between areas A and C is determined to reach 10 mV in step S17.

Figure 8:
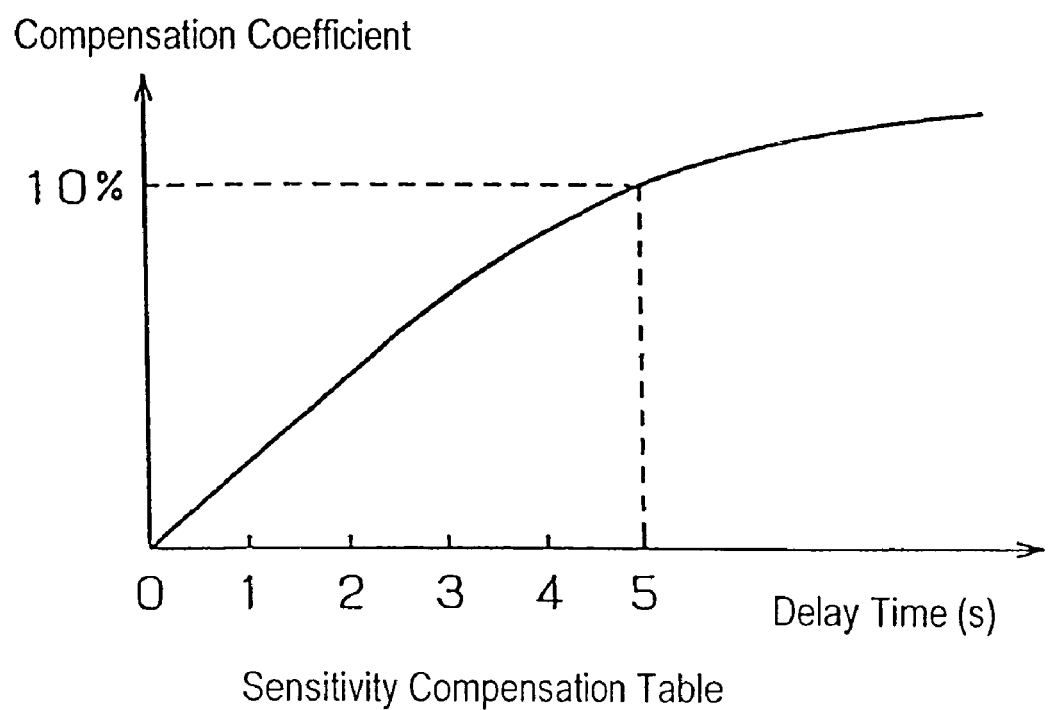
FIG. 8 illustrates a relation between a delay time and a compensation coefficient for compensating a measured quantity of a substrate.

FIG. 8 is a sensitivity compensation table illustrating a relation between the delay time and a compensation coefficient for the measured quantity of the substrate. The vertical axis represents the compensation coefficient, and the horizontal axis represents the delay time. For instance, if the delay time is 5 seconds, the measured quantity is compensated by 10% lower. As a result, 90% of the measured quantity becomes a compensated quantity. This kind of the sensitivity compensation table is stored in a memory (not shown). of measuring device 10, and this table is referred when a final quantity of the substrate is calculated.

Figure 2:
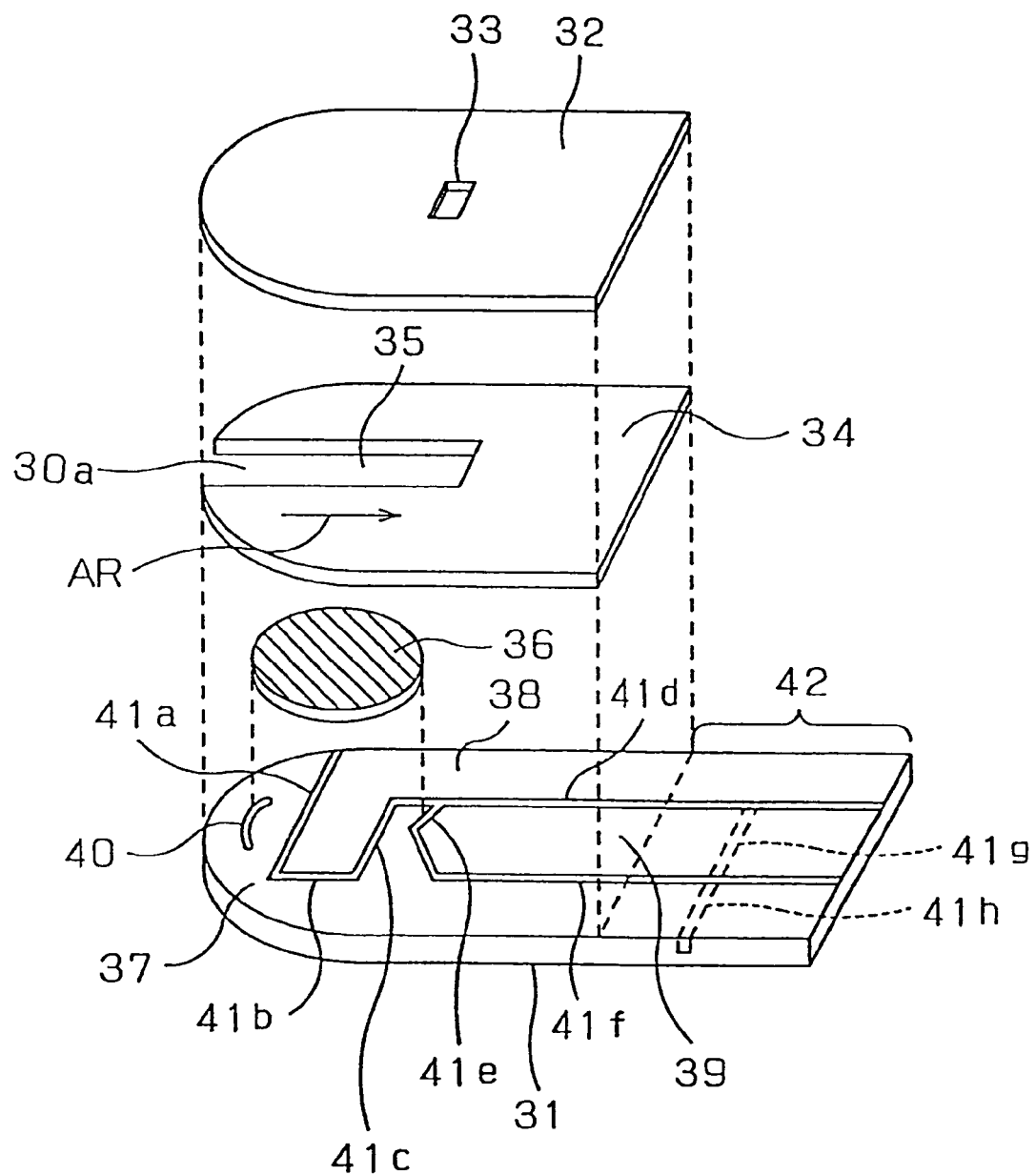
FIG. 2 is an exploded perspective view of a biosensor in accordance with a first exemplary embodiment of the present invention.

In biosensor 30 shown in FIG. 2, counter electrode 37 is formed such that slit 41f extends toward slit 41c and connects with slit 41b. Then a drip position error caused through dripping the sample liquid to air hole 33 by mistake, can be detected. In the flowchart shown in FIG. 6, if the voltage measured between areas A and C is determined to excess 10 mV not the voltage between areas A and E (step S15: Yes), it is determined, in 0.2 seconds after the determination, whether or not the voltage between areas A and E reaches 10 mV (step S20). If the voltage between areas A and E does not excess 10 mV, it is determined that the sample liquid has been dripped to an incorrect position, and the measuring process terminates (step S50).

If the sample liquid is normally dripped on sample-drip point 30a, the liquid is sucked along sample supplying path 35 to air hole 33 and then moistens counter electrode 37, measuring electrode 38 and detecting electrode 39 in this order. However, if the voltage measured only between areas A and C changes largely, a user has probably dripped the sample liquid to air hole 33 incorrectly. In this case, it is determined that an exact measurement is not expected, and the measuring process compulsorily terminates due to an error of dripping at a incorrect position. This can avoid a measurement error due to an incorrect operation by the user.

If the voltage measured between areas A and C is determined to reach 10 mV (step S17: Yes), or if the voltage measured between areas A and E is determined to reach 10 mV (step S20: Yes), enough quantity of the sample liquid is determined to be dripped. Then a pre-process for measuring the quantity of the substrate starts, and a timer (not shown) of measuring device 10 counts time (step S21).

Next, conductivity between areas A and F is tested (step S22). Switch 22 is turned on, and the conductivity is tested between areas A and F. If the conductivity is detected (step S22: Yes), it is determined whether result I identifying a type of biosensor 30 is stored in the memory in step S9 or not (step S23). If result I is stored (step S23: Yes), it is determined that the type of biosensor 30 is that shown in FIG. 3(g). Calibration curve data is prepared using voltages measured when the reduced electron acceptor is oxidized electrochemically. Then calibration curve F7 is prepared as the calibration curve data for specifying a concentration of the glucose in the sample liquid (step S24).

On the other hand, when result II is stored (step S23: No), it is determined that the type of biosensor 30 is that shown in FIG. 3(e), and calibration curve F5 is prepared as the calibration curve data (step S25). If the conductivity is not detected between areas A and F (step S22: No), it is determined that the type of biosensor 30 is that shown in FIG. 3(f), and calibration curve F6 is prepared as the calibration curve data (step S26).

As discussed above, a difference in output characteristics of biosensor 30 is automatically recognized responsive to the slits in recognizing section 42 of biosensor 30. The calibration curve data appropriate to the output characteristics is then automatically selected and set. Therefore, a user does not need a compensating chip, and CPU 25 switches automatically the calibration curve data to which the output characteristics depending on production lots are reflected. As a result, an incorrect measurement using user's incorrect data can be avoided, and a highly accurate measurement can be expected.

After the calibration curve is prepared in steps S24 to S26, the measuring pre-process starts (step S27-S29). The pre-process will be demonstrated with reference to FIG. 9, which illustrates a profile of the pre-process in accordance with the first embodiment.

Figure 9:
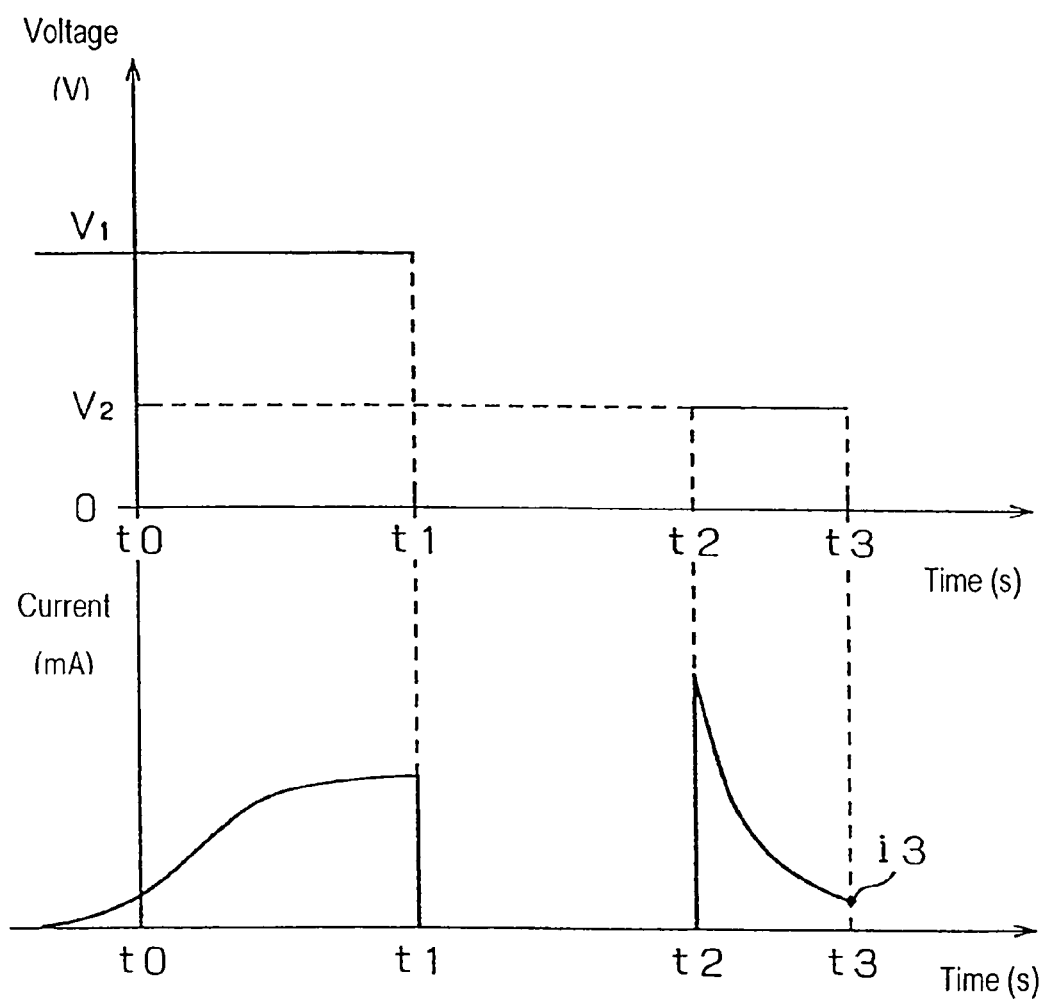
FIG. 9 shows a profile at a measurement pre-process.

In the profile shown in FIG. 9, the pre-process starts at time t0. Specifically, time t0 is the time when the timer (not shown) of measuring device 10 starts counting time. The profile of the pre-process includes three consecutive periods, for instance, a first voltage period t0-t1, a standby period t1-t2, and a second voltage period t2-t3.

During the first voltage period, voltage V1 is applied to areas A, C and E, to have the enzyme reaction progress. This increases a voltage measured by oxidizing ferrocyanide electrochemically similar to an exponential function. Next, during the standby period, voltage V1 applied during the first voltage period is set at zero, and thus the ferrocyanide is not oxidized electrochemically, but the enzyme reaction keeps progressing. The ferrocyanide is thus accumulated. During the second voltage period, voltage V2 is applied to areas A, C and E to oxidize the ferrocyanide accumulated during the standby period all at once. Then a quantity of discharged electron increases, and a high response current is thus observed at time t2. A current reaching the high response current decreases, as time passes, into a stable value i3 at time t3. In the pre-process, switches 19 and 21 are simultaneously turned on in measuring device 10, so that a voltage is applied to counter electrode 37 and detecting electrode 39 as one unit.

Recently, shortening a measurement time has been desired to upgrade a performance of the biosensor. When a quantity of a substrate is measured with a biosensor, a viscosity of the sample liquid critically influences measurement accuracy. This was found by the inventor. In particular, when human blood is measured as the sample liquid, blood with high viscosity (high Hct) lowers measurement sensitivity, and blood with low viscosity (low Hct) increases the measurement sensitivity. This phenomenon derives from a dissolving speed of a reagent layer in the blood, i.e., slow dissolution in high Hct and quick dissolution in low Hct. Thus the viscosity influences the measurement sensitivity of the biosensor.

Figure 10:
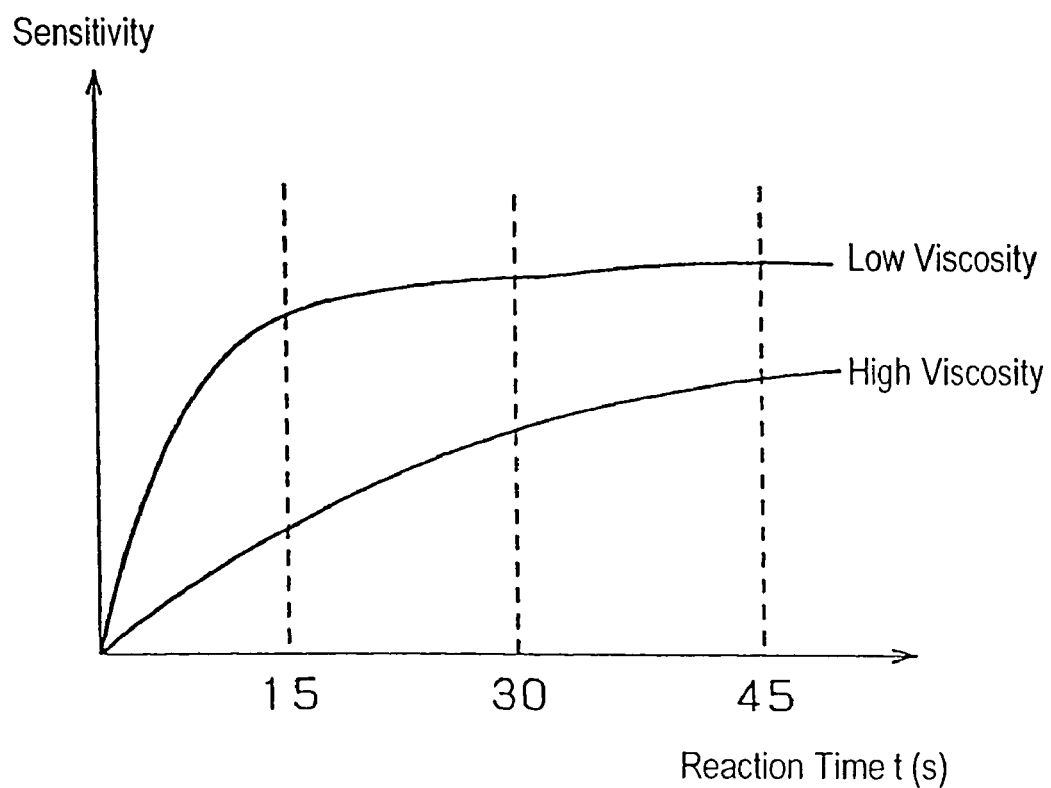
FIG. 10 shows a relation between a blood viscosity, a reaction time of reactive reagent layer and blood, and a measurement sensitivity.

FIG. 10 shows a relation between a blood viscosity, a reaction time of reactive reagent layer on the blood, and a measurement sensitivity. Data shown in FIG. 10 is measured by a conventional method, which applies a voltage within a period corresponding to the second voltage period shown in FIG. 9 and measures the voltage. As shown in FIG. 10, influence due to differences in viscosity (Hct in the case of blood) to measurement sensitivity increases at a shorter reaction time. Great difference is observed between the high Hct and the low Hct particularly at a reaction time around 5 sec.

Therefore, the conventional method tends to reveal a measurement error obviously due to blood viscosity.

During the first voltage period of the pre-process, reaction products produced at an initial stage of dissolving reagent layer 36 is thus compulsorily consumed by applying voltage V1. During the first voltage period, since the low Hct has a higher speed in enzyme reaction than the high Hct, greater reaction products are produced in the low Hct and thus greater reaction products are consumed. However, if a voltage is applied for too long period, reaction products are consumed too much, and responsivity of a voltage detected in the second voltage period may probably decline. Therefore, an effective first voltage period t1-t0 may be 3 to 13 seconds. The voltage to be applied may be further increased, so that a voltage application time is preferably 2 to 10 seconds. Voltage V1 may range preferably from 0.1 to 0.8V.

Next, during the standby period, the enzyme reaction progresses again, and the reaction products in the low Hct blood, the reaction products which have been consumed in the first voltage period, are quickly recovered and accumulated in approximately the same quantity as those in the high Hct blood. Too long a standby period or too short a standby period influences the final measurement sensitivity in a different way.

If the standby period is too short, a response value i3 measured at time t3 becomes too low, and a measurement error becomes great. If the standby period is too long, a difference in enzyme reaction speed between the low Hct blood and the high Hct blood probably becomes greater. The standby period is determined so that the difference in enzyme reaction speeds may not become greater. As a result, the standby period t2-t1 is 1 to 10 seconds and preferably 2 to 10 seconds.

During the second voltage period, voltage V2 starts being applied at time t2. And just after time t2, the voltage is not stable and requires a time to be stable. A voltage similar to that during the first voltage period is not necessarily applied, and a lower voltage than voltage V1 is preferably applied. The lower voltage may be low enough to oxidize ferrocyanide kalium. The second voltage period t3-t2 is thus preferably 2 to 10 seconds. Voltage V2 is preferably 0.05 to 0.6V. Finally, value i3 measured between areas A, C and area E at time t3 is read out, and the quantity of the substrate (glucose) in the sample liquid is calculated.

The set time discussed above is particularly suitable for a quantity measuring with the biosensor including electrodes made of noble metal such as palladium. A reagent is not limited to glucose oxidase and/or glucose dehydrogenase and ferricyanide kalium, but includes amino acid, sugar alcohol. The set time is also suitable to a biosensor including organic acid.

After the sample liquid is supplied to sample supplying path 35, the reaction of reagent layer 36 in the sample liquid is incubated in a certain period before the quantity of the substrate is measured. The incubate period may change depending on the laps of time since the voltage measured between areas A and E exceeds a threshold (10 mV) in step S14 until the voltage between areas A and C exceeds the threshold (10 mV) in step S17.

Figure 11:
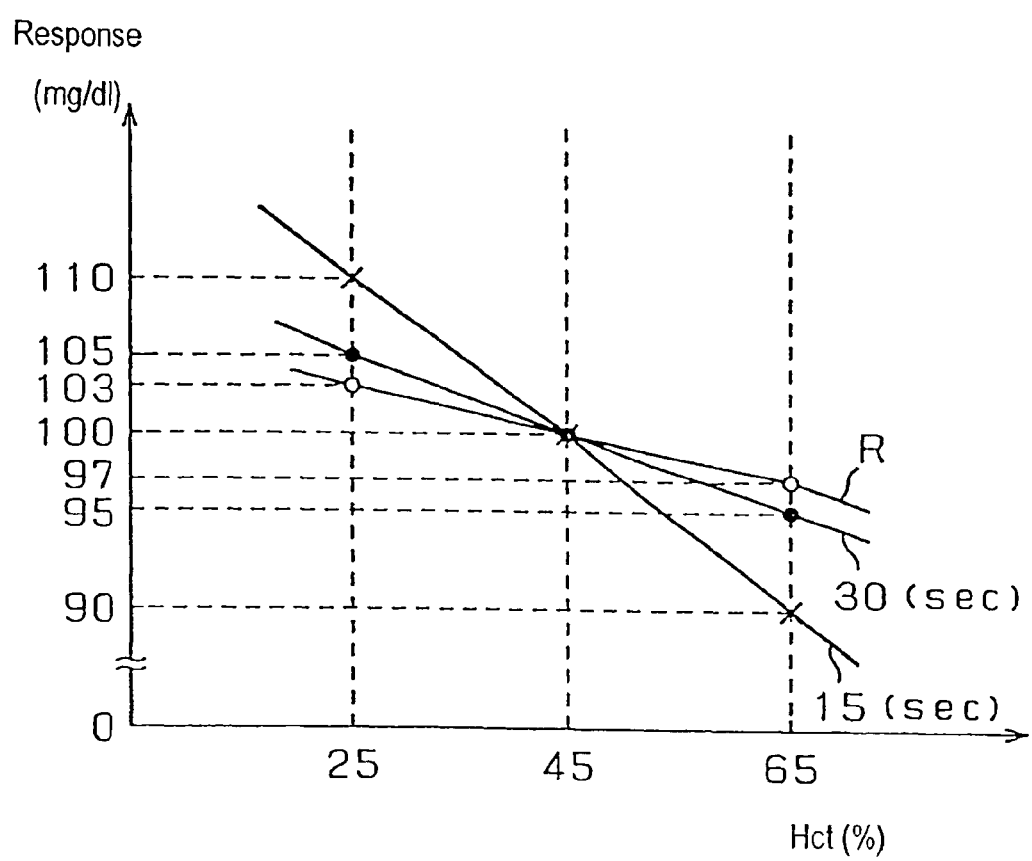
FIG. 11 shows a glucose concentration (mg/dl) measured by a conventional method and a measurement pre-process of the present invention.

FIG. 11 shows glucose concentrations (mg/dl) measured by the conventional method and the measuring pre-process discussed above for three types of blood having contents of hematocrit (Hct) of 25%, 45% and 65%. Reference mark R in FIG. 11 denotes the measurement result by the pre-process. The other two results were measured by the conventional method with 15 seconds and 30 seconds of the reaction time. The pre-process was performed under the following condition: the first voltage period was 6 seconds; voltage V1 was 0.5V; the standby period was 6 seconds; the second voltage period was 3 seconds; and voltage V2 was 0.2V. As compared with a measurement for: the Hct was 45%; and the glucose concentration was 100 mg/dl, an actual measurement proved that low Hct (25%) blood and high Hct (65%) blood produce greater dispersion in the measurement, and the response values of low Hct disperse in a higher range and those of high Hct disperse in a lower range. Further, the dispersion becomes greater at a shorter reaction time. At a reaction time of 15 seconds, the dispersion is produced by 10% higher (low Hct of 25%) and by 10% lower (high Hct of 65%). At a reaction time of 30 seconds, the dispersion is produced by 5% higher (low Hct of 25%) and by 5% lower (high Hct of 65%). In this pre-process, the dispersion is produced by 3% higher (low Hct of 25%) and by 3% lower (high Hct of 65%). At a reaction time of 15 seconds, FIG. 11 teaches that the pre-process can reduce the dispersion due to the types of Hct while the reaction time is the same as that in the conventional method.

Back to FIG. 7 again, the description of the measuring process continues hereinafter. The measuring pre-process starts, and 0.5V is applied between areas A and C, and between areas A and E for 6 seconds in the first voltage period (step S27). After the first voltage period, the standby period is taken for 6 sec., and the voltage applied is cancelled in the standby period (step S28). After the standby period, the second voltage period starts, and 0.2V is applied between areas A and C, and between areas A and E for 3 sec. (step S29). Then value i3 is read out (step 30).

After value i3 is read out in step S30, temperature measuring sections 26 and 28 and switches 27, 29 disposed in measuring device 10 are controlled to measure a temperature in measuring device 10 (step S31). Specifically, switch 27 is turned on, and measuring section 26 measures the temperature (step S31). Then switch 27 is turned off, switch 29 is turned on, and measuring section 28 measures the temperature (step S32).

The two temperatures measured by temperature measuring section 26 and 28 are compared with each other, and it is determined whether or not the difference between the two temperatures ranges within a given threshold (step S33). If the difference is out of the threshold, the measuring process terminates due to a failure of either one of measuring section 26 or 28 (step S33: No). As such, plural temperature-measuring sections (26, 28) are disposed in measuring device 10, and their measuring results are compared, so that a failure can be detected exactly and easily. This can avoid a measurement error caused by a measurement at an irregular temperature. The temperatures are measured just after the value has been read out in step S30; however, the temperatures may be measured, for instance, when the pre-process starts in step S21. If the difference between the two temperatures measured ranges within the given threshold (step S33: Yes), the temperatures are temporarily stored in a memory (not shown). At this time, the temperature measured by either one of sections 26 or 28 may be selected and stored, and the average of the two temperatures may be stored. Then a calibration curve, which should refer to value i3 measured in step S30, is specified (step S34). The calibration curves prepared in steps S24, S25 and S26 are referred. If biosensor 30 corresponds to step S24, calibration curve F7 is referred (step S35). In the same manner, if biosensor 30 corresponds to step S25, calibration curve F5 is referred (step S36). If biosensor 30 corresponds to step S26, calibration curve F6 is referred (step S37).

FIG. 12 shows calibration curve data CA measured in steps S34, S35 and S36. In data CA, a voltage measured in step S30 and a concentration (mg/dl) of a substrate included in sample liquid are determined depending on each output characteristic F1 to F7 of biosensor 30. For instance, if a measured voltage is 25 mV, and the biosensor corresponds to calibration curve F5, a substrate concentration of 14 (mg/dl) is stored in the memory.

Next, a concentration of the substrate selected in step S35, S36 or S37 is compensated by a compensation coefficient corresponding to the delay time which has been found in steps S14 and S17 and stored in the memory (step S38). Specifically, the concentration is compensated by the following equation (1):

$$D1 = (\text{concentration of substrate}) \times [\{100 - (\text{sensitivity compensation coefficient})\}/100]$$

where D1 is a compensated concentration of the substrate. This compensation eliminates a measurement error due to adding sample liquid by a user.

Next, the concentration compensated in step S38 is compensated according to the temperatures measured in steps S31 to S33 (step S39). The temperature stored in the memory in step S33 is read out, and a temperature compensation table shown in FIG. 13 is referred, thereby determining a temperature compensation coefficient to be applied to concentration D1.

FIG. 13 shows temperature compensation tables. Compensation table T10 is used for the temperature of 10° C. In the same manner, table T15 is for the temperature of 15° C., and table T20 is for the temperature of 20° C. The compensation tables specifies a relation between substrate concentration D1 in the sample liquid and a temperature compensation coefficient is specified. The temperature compensation coefficient is determined based on a concentration at 25° C. as a reference, and shows a coefficient for compensation with respect to the concentration. Specifically, the compensation for temperature is performed according to the following equation (2):

$$D2 = D1 \times (100 - Co)/100$$

where D2 is a compensated concentration, D1 is the concentration calculated in step S38, and Co is the temperature compensation coefficient specified by referring to the temperature compensation table.

Figure 14:
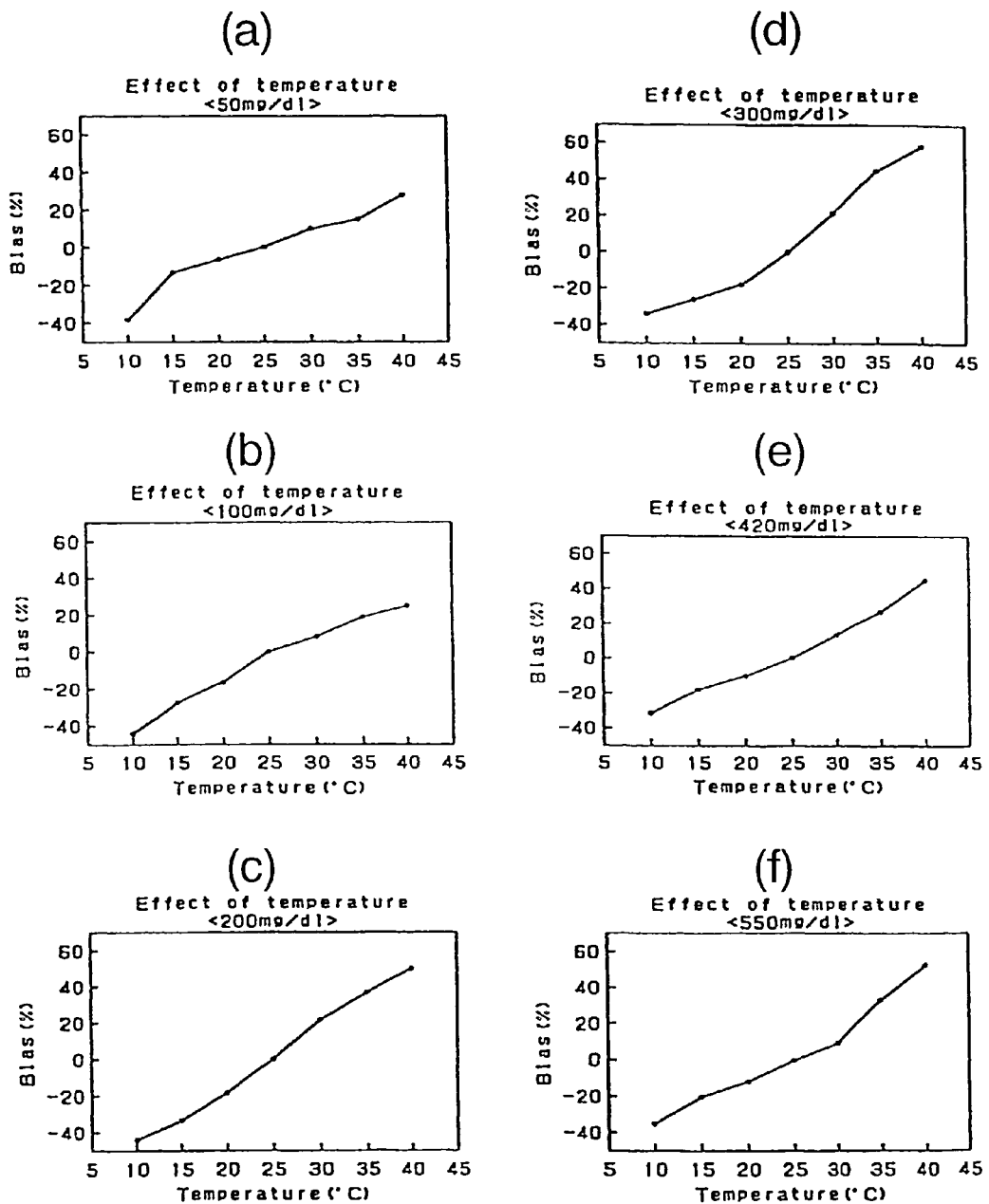
FIG. 14 shows relations between a temperature measured and measurement dispersion at each concentration of a substrate.

The inventors found experimentally that measurement accuracy was influenced by a combination of a measured temperature and a concentration of a substrate. The influence will be described hereinafter. FIG. 14 shows relations between the measured temperature and measurement dispersion (bias) at each concentration of glucose. The measurement dispersion in FIG. 14 is defined by a coefficient of a change of a concentration of glucose measured at 25° C. according to a change of the measured temperature. FIG. 14(a) shows a relation between the dispersion and the measured temperature in the case of glucose concentration of 50 mg/dl at 25° C. Similarly, FIG. 14(b) shows the relation for the glucose concentration of 100 mg/dl and the temperature of 25° C. FIG. 14(c) shows the relation for the glucose concentration of 200 mg/dl and the temperature of 25° C. FIG. 14(d) shows the relation for the glucose concentration of 300 mg/dl and the temperature of 25° C. FIG. 14(e) shows the relation for the glucose concentration of 420 mg/dl and the temperature of 25° C. FIG. 14(f) shows the relation for the glucose concentration 550 mg/dl and the temperature of 25° C.

These experimental data point out the following two tendencies. First, for the same glucose concentration, the measuring dispersion increases as a difference between a measured temperature and reference temperature 25° C. becomes greater. In detail, the dispersion increases in a negative direction as a measured temperature decreases from the reference temperature, and the dispersion increases in a positive direction as a measured temperature rises from the reference temperature. Second, the dispersion converges at the glucose concentration of 300 mg/dl, which seems a boundary, even though the glucose concentration increases. Specifically, FIG. 14(a) indicates the dispersion of approximately 28% at 40° C., FIG. 14(c) indicates approximately 50%, FIG. 14(d) indicates approximately 60%, and FIG. 14(f) indicates approximately 50%. A similar tendency is found in a low temperature range such as a measured temperature of 10° C.

This tendency is reflected to the tables shown in FIG. 13. First, the measuring dispersion increases as a difference between a measured temperature and reference temperature of 25° C. becomes greater for the same glucose concentration. Second, the dispersion starts converging at the glucose concentration of 300 mg/dl as a boundary even though the glucose concentration increases. These two aspects are taken into consideration for preparing the tables. The measurement accuracy is remarkably improved by compensating a concentration referring to the temperature compensation table, in which combinations of measured temperatures and concentrations of the substrate are well considered, rather than compensating a concentration only based on a measured temperature.

In an operable temperature range of biosensor 30 (10° C. to 40° C. in this embodiment), a temperature compensation table for every 1° C. may be prepared, or the table for every given temperature range (e.g. 5° C.). If a temperature at a middle of the given temperature range is detected, a temperature compensation coefficient may be calculated by a linear interpolation with a temperature compensation table including the detected temperature.

Back to the flowchart in FIG. 7, concentration D2, which has undergone the temperature compensation discussed above, is output on display 11 of measuring device 10 as a final concentration of the substrate (step S40). As discussed above, the time when the sample liquid is added, the measured temperature, and the combination of the measured temperature and the concentration are considered as influence factors to the measurement. A viscosity (Hct) of sample liquid is also considered as an influence factor. Those factors are taken into consideration when the quantity of a substrate is measured. As a result, the measurement accuracy is remarkably improved from the measurement by a conventional method.

The following method can be introduced in order to further decrease a measurement error due to temperature.

Before biosensor 30 is inserted into measuring device 10, the temperature is measured successively and stored. After biosensor 30 is inserted, temperatures measured in steps S31 and S32 are compared with the stored ones. If large differences between the stored temperatures and the measured ones are found, the measuring process may compulsorily terminates due to a significant temperature change which influences a measurement error.

A portable biosensor system in accordance with this first embodiment, being carried easily, is exposed in various temperature changes depending on the outside environment. For instance, the biosensor system may be influenced by a temperature of a user's hand, or a sharp change in temperature when a user moves from outside to indoors. The sharp temperature-change can be expected, it takes reasonable time for measuring device 10 to be stabilized in its temperature change.

Figure 15:
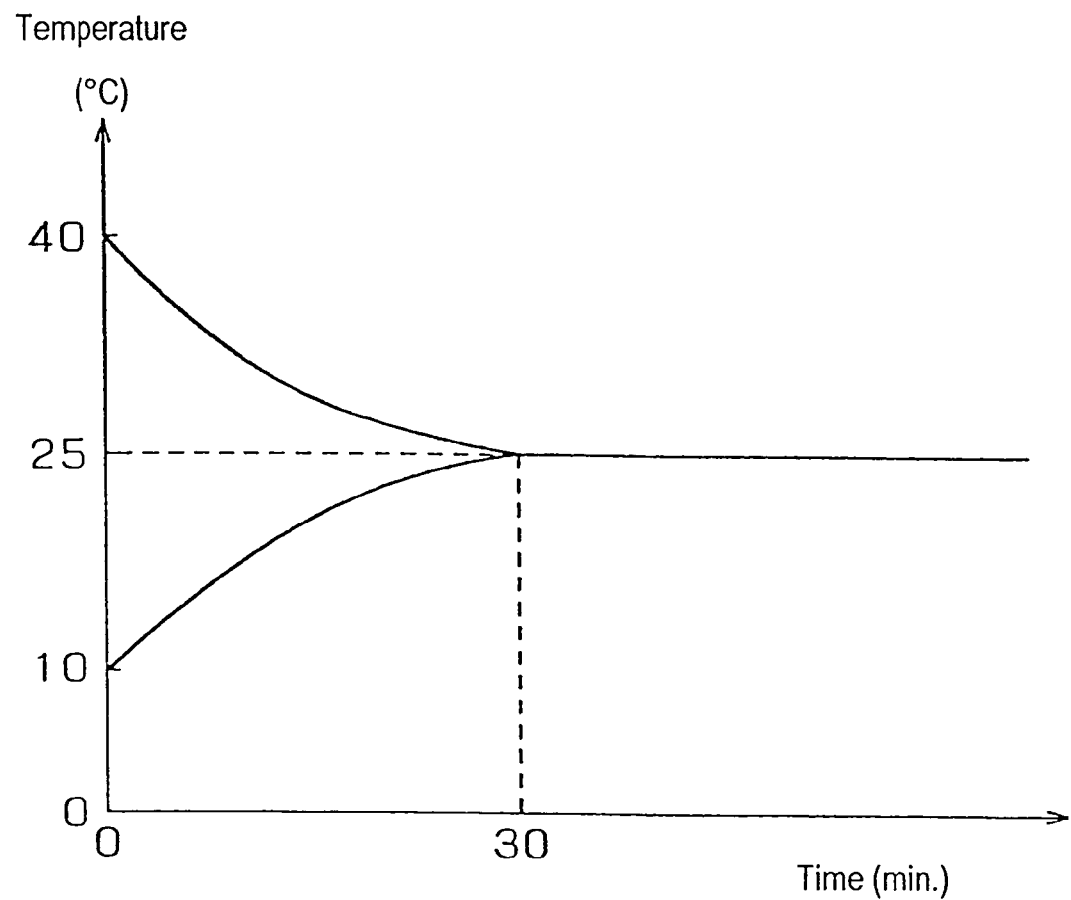
FIG. 15 shows a temperature change in a measuring device.

FIG. 15 shows temperature changes in measuring device 10. A temperature change in device 10 moving from a place at a temperature of 10° C. to another place at a temperature of that of 25° C. is shown in FIG. 15. A temperature change in device 10 moving from a place at a temperature of 40° C. to a place of a temperature of 25 C. is also shown in FIG. 15. FIG. 15 shows that it takes approximately 30 minutes to stabilize the temperature changes in an ambient temperature ranging from 10 to 40° C. If the temperature compensation is carried while the temperature changes, an exact temperature compensation may not be expected.

Therefore, if a great difference between the temperature stored in advance and the temperatures measured in steps S31 and S32, the measuring process may compulsorily terminate due to the temperature change which may influence a measuring error. This further improves the accuracy of temperature compensation in measuring device 10. A temperature may be measured before biosensor 30 is inserted into measuring device 10 at given intervals, e.g., 5-minute interval, or successively. Based on the magnitude of temperature change, the measuring process may be cancelled although a user tries to carry it out.

Exemplary Embodiment 2

The biosensor in accordance with the second exemplary embodiment will be demonstrated hereinafter. In this embodiment, an enzyme sensor is described. The sensor employs an enzyme as a molecule recognizing element which specifically reacts on a specific material contained in sample liquid.

An incorrect operation by a user influences a measuring accuracy. Thus the second embodiment discusses this problem. In particular, a user fails to drip sample liquid to an inlet of a sample supplying path, and the sample liquid attaches to a surrounding areas of the inlet. As a result, the sample supplying path cannot carry the sample liquid. Such kind of incorrect operations by a user may affect a measurement accuracy, and the ways how to avoid those mis-operations are demonstrated in this embodiment.

Figure 16:
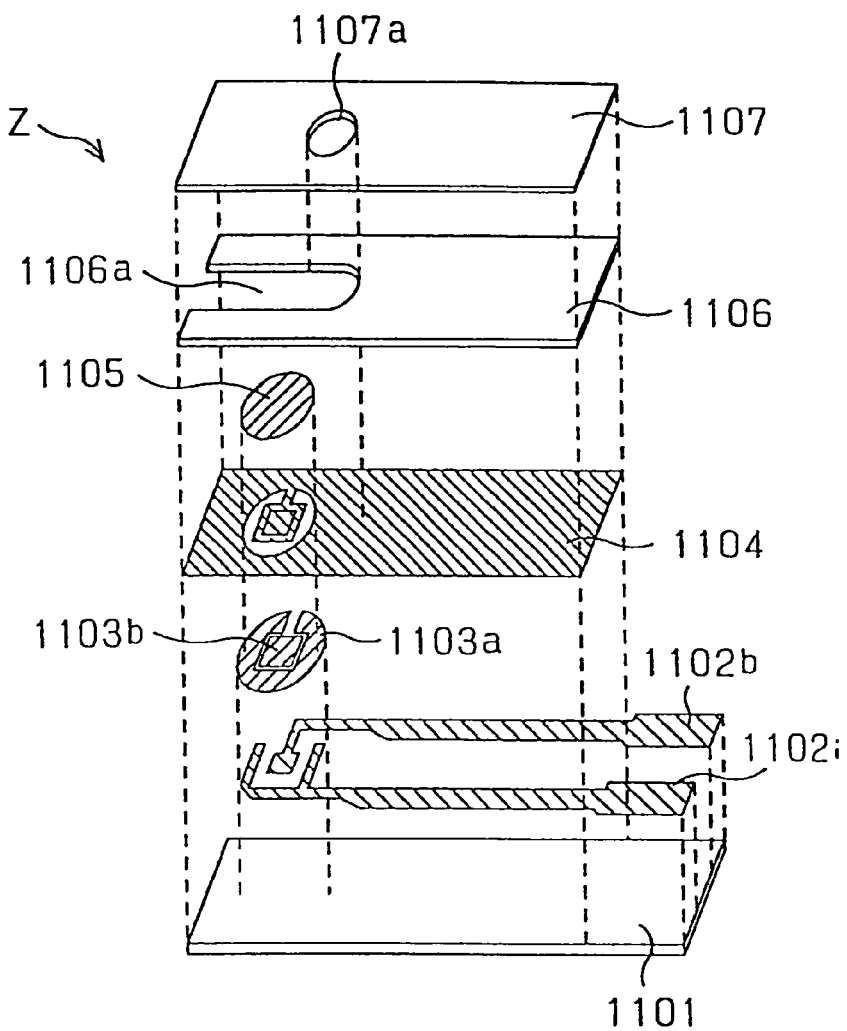
FIG. 16 is an exploded perspective view of a conventional biosensor.
Figure 16:
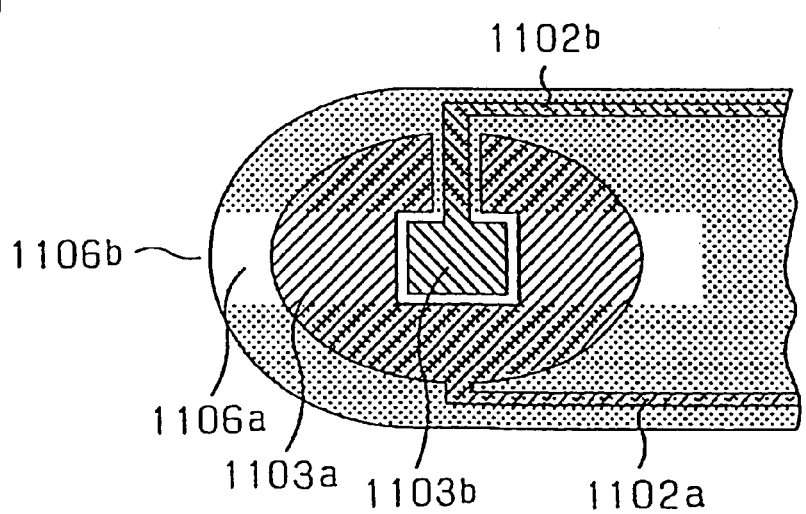

According to a structure shown in FIG. 16 or FIG. 2, at the inlet, to which sample liquid is supplied, of the sample supplying path, an insulating board and a cover forming the path have respective ends of the same shape at the same location in a plan view. Therefore, a sample supplying angle becomes small. Or when the sample liquid attaches to a rear side (a side having no electrode formed thereon) of the insulating board by mistake, this sample liquid attached to the rear side may prevents the user from again supplying the sample liquid. As a result, the sample liquid is not supplied well, which causes a failure in measurement or a measurement error.

Figure 17:
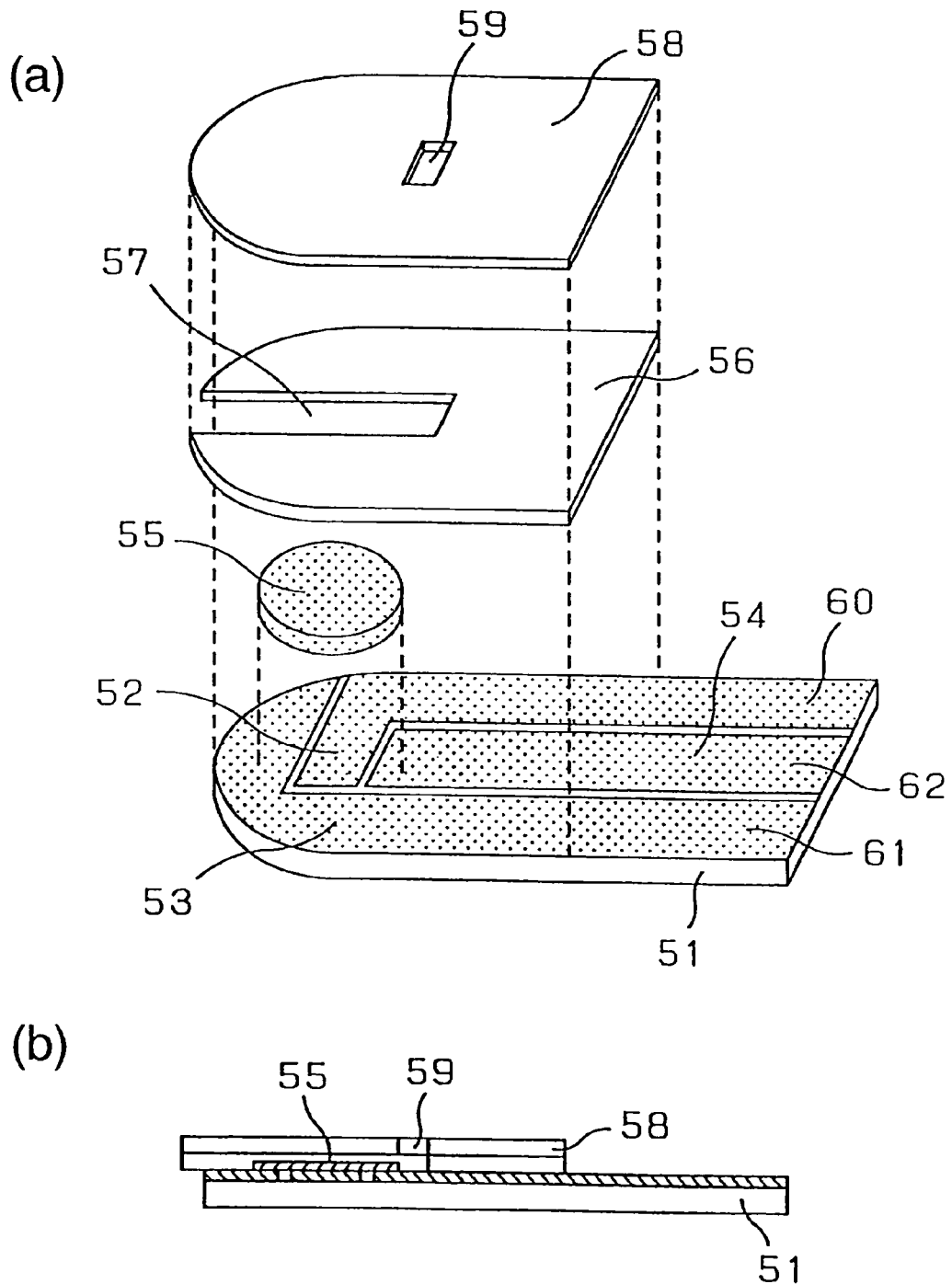
FIG. 17 shows an exploded perspective view and a sectional view of a biosensor in accordance with a second exemplary embodiment of the present invention.

A biosensor which can accept the sample liquid exactly and easily will be specifically described hereinafter. FIG. 17(*a*) is an exploded perspective view of the biosensor in accordance with the second embodiment. FIG. 17(*b*) is a cross section at a center of the sample supplying path in the longitudinal direction of the biosensor. In FIG. 17, measuring electrode 52, counter electrode 53 and detecting electrode 54 are formed on first insulating board 51. Those electrodes are made of electrically conductive material. Detecting electrode 54 in this embodiment functions not only as an electrode for detecting a insufficiency of a specimen but also as a part of a reference electrode or as a part of the counter electrode.

FIG. 17 shows that the electrodes discussed above are disposed on the first insulating board; however, those electrodes may be divided and disposed also on second insulating board 58 to be a cover board located opposite to first board 51.

Boards 51 and 58 are preferably made of polyethylene terephthalate, polycarbonate, polyimide or the like.

Each electrode is preferably made of electrically conductive material such as noble metal including gold, platinum, and palladium, or simple material such as carbon. They may be also made of composite material such as carbon paste or noble metal paste. In the former case, a conductive layer can be formed on board 51 or 58 easily by a sputtering evaporation method. In the latter case, a conductive layer can be formed on board 51 or 58 easily by a screen printing method.

The conductive layer is formed on an entire or a part of first insulating board 51 or second insulating board 58 by the sputtering evaporation method or the screen printing method. Then slits are provided by laser for forming and dividing the electrodes. The electrodes may be formed by the screen printing method or a sputtering evaporation method on a printed board or a masked board having electrode patterns formed in advance.

On the electrodes thus formed, reagent layer 55 is formed. Reagent layer 35 includes enzymes, electron carriers and hydrophilic high-polymer. The enzymes include glucose oxidase, lactate oxidase, cholesterol oxidase, cholesterol estrase, uricase, ascorbate acid oxidase, billrubin oxidase, glucose dehydrogenase, lactate dehydrogenase. The electron carrier preferably employ ferricyanide kalium and may employ p-benzoquinone and its derivatives, phenacine methor sulphate, methylene blue, or pherocane and its derivatives.

The hydrophilic high-polymer employ, e.g. carboxymethyl cellulose, hdroxy-ethyl cellulose, hydroxy propyl cellulose, methyl cellulose, ethyl cellulose, ethyl hydroxyethyl cellulose, carboxy methyl ethyl cellulose, polyvinyl alcohol, polyvinyl pyrrolidone, polyamino acids such as poly-lysine, sulfonated polystyrene acid, gelatin and its derivatives, acrylic acid and its salts, methacrylic acid and its salts, starch and its derivatives, anhydrous maleci acid and its salts, or agarose gel and its derivatives.

First insulating board 51 and second insulating board 58 are bonded via spacer 56 in between for forming sample supplying path 57, from which sample liquid is supplied. Spacer 56 has slit-shaped notch 57 formed therein.

A significant difference from the conventional biosensor is that first board 51 and second board 58 forming path 57 are placed with their ends at an inlet of sample supplying path 57 deviated each other and bonded. That is, respective ends are placed at different places from each other. This preparation is viewed from a plan view. In other words, first board 51 and second board 58 are in the same shape near the inlet of path 57; however, second board 58 and spacer 56 protrude toward the inlet with respect to first board 51.

This allows the sample liquid to be sucked exactly and easily even though the sample supplying angle is small. This prevents the sample liquid from attaching to the rear side of first board 51. Even if the sample liquid attaches to the rear side, the sample liquid can be supplied again smoothly.

Figure 18:
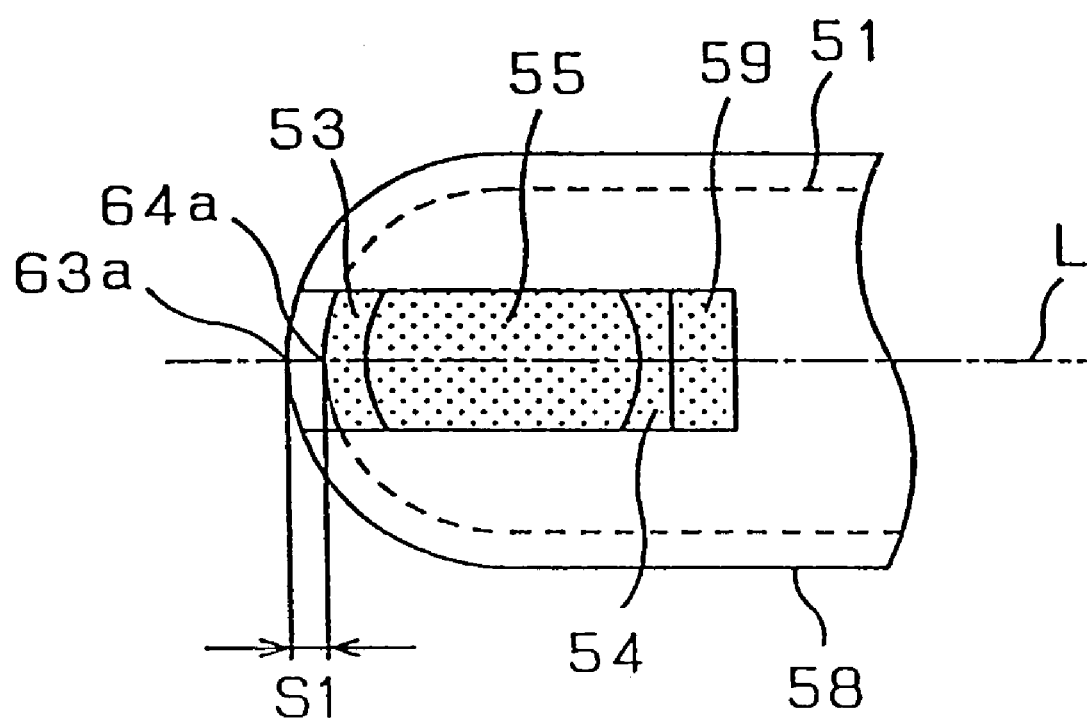
FIG. 18 is an enlarged plan view illustrating a sample supplying path of the biosensor shown in FIG. 17.

The deviation of second board 58 from first board 51 at the ends thereof, that is, distance S1 between points 63*a* and 64*a* is preferably not less than 0.1 mm and more preferably ranges from 0.25 to 1.0 mm, where center line L of path 57 shown in FIG. 18 crosses with first board 51 and second board 58 at points 64*a* and 63*a*, respectively.

If being less than 0.1 mm, distance S1 is too short. The sample liquid thus cannot be supplied well if the sample supplying angle is small as in the conventional biosensor.

Figure 19:
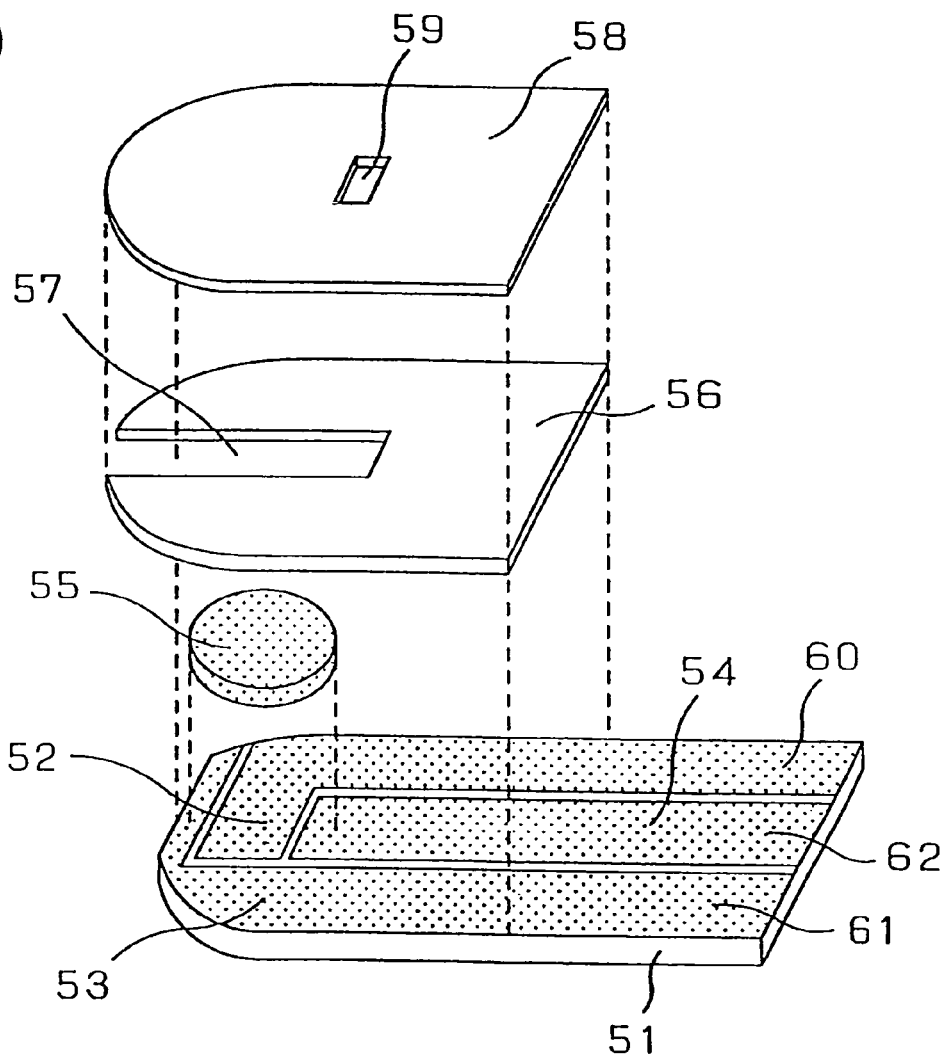
FIG. 19 shows an exploded view and a sectional view of another example of the biosensor.
Figure 19:
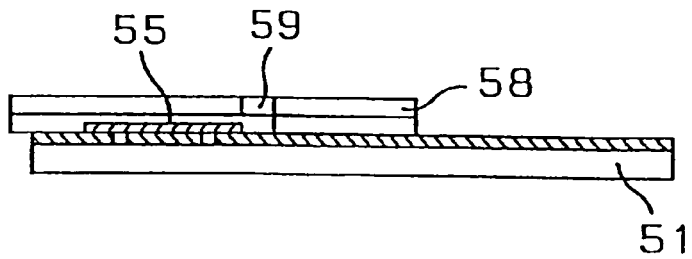
Figure 20:
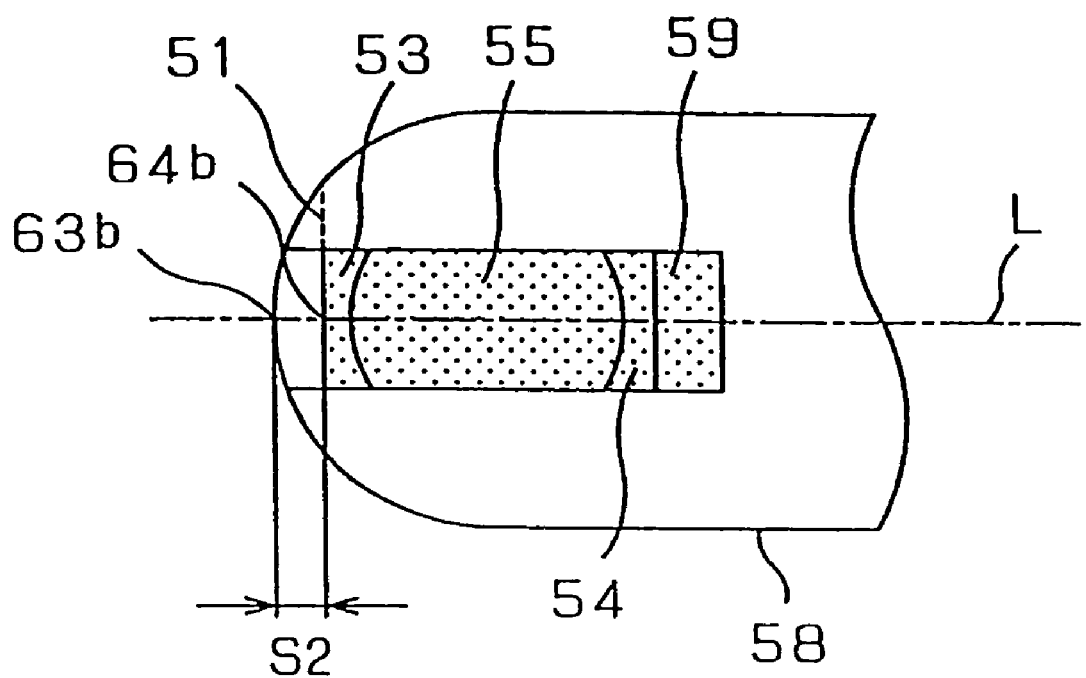
FIG. 20 is an enlarged plan view illustrating a sample supplying path of the biosensor.

If first board 51 has different shape from second board 58 near the inlet of path 57 as shown in FIG. 19, a similar advantage to that discussed above is measurable. In this case, the deviation at the ends thereof, i.e., center line L of path 57 shown in FIG. 20 crosses with first board 51 at point 64*b* and crosses with second board 58 at point 63*b*. Distance S2 between point 63*b* and point 64*b* is preferably not less than 0.1 mm and more preferably ranging from 0.25 to 1.0 mm.

In the structures illustrated in FIG. 17 to FIG. 20, a depth of the sample supplying path, i.e., a thickness of spacer 56, ranges preferably from 0.05 to 0.3 mm in order to supply the sample liquid quickly to slit-shaped path 57.

Spacer 56 is preferably made of polyethylene terephthalate, polycarbonate, polyimide, polybutylene terephthalate, polyamide, polyvinyl chloride, polyvinylidene chloride, or nylon.

For form sample supplying path 57, first board 51 may be bonded to second board 58 integrated with spacer 56 into one unit.

Reagent layer 55 is disposed on entire or a part of a surface of the electrode, and however, may be disposed anywhere in sample supplying path 57 as long as it does not lower the performance of the biosensor. The sample liquid is supplied to the biosensor through path 57 having a structure discussed above by the capillary phenomenon. However, air hole 59 through which air flows outside the biosensor is necessary in path 57 in order to supply the sample liquid smoothly. Air hole 59 may shape in a rectangle, circle or polygon.

Air hole 59 may be located anywhere in path 57 as long as it does not block the supply of sample liquid.

Hydrophilic treatment which may be performed inside path 57 enables the sample liquid to be supplied into path 57 more quickly and accurately. The hydrophilic treatment is realized by developing surface active agent into or on second board 58, or by roughing the surface of the board by sandblasting, electric-discharge machining, non-glare process, mat process, or chemical plating.

In the biosensor discussed above, a current is generated by the reaction between a specific component in the sample liquid and reagent layer 55 containing enzymes. The current is conducted to an external measuring instrument (not shown) via lead-wires 60, 61, and 62 of measuring electrode 52, counter electrode 53, detecting electrode 54 for being measured.

For the current measurement, a triple-electrode method employing measuring electrode 52, counter electrode 53 and detecting electrode 54 is available as discussed in this embodiment. Besides the triple-electrode method, a double-electrode method employing only measuring electrode 52 and counter electrode 53 is available. Either method can produce the similar advantage to that of this embodiment; however, the triple-electrode method achieves more precise measurement.

EXAMPLE 1

A thin palladium film of 8 nm thickness was formed on the entire surface of the first insulating board made of polyethylene terephthalate by sputtering evaporation method. Then slits were provided on a part of the thin film by YAG laser, and thus the electrode was divided into a measuring electrode, a counter electrode and a detecting electrode. On top of that, water solution containing enzymes, electron carriers, and hydrophilic high-polymer was dripped such that the water solution covered the measuring electrode as a center and parts of the counter electrode as well as the detecting electrode. Then the water solution was dried to form a reagent layer. Further on top of that, a spacer made of polyethylene terephthalate and having a notch together with the second insulating board (cover) made of polyethylene terephthalate and having the air hole was bonded. As a result, the sample supplying path, i.e., a capillary which leads blood, was formed.

In order to confirm the advantage of the present invention, the following six types of blood-sugar value sensors having end-deviations (distance S) from the board to the spacer and cover were determined as: S=0 (a conventional sensor), 0.1, 0.25, 0.5, 1.0, and 2.0 mm.

Figure 21:
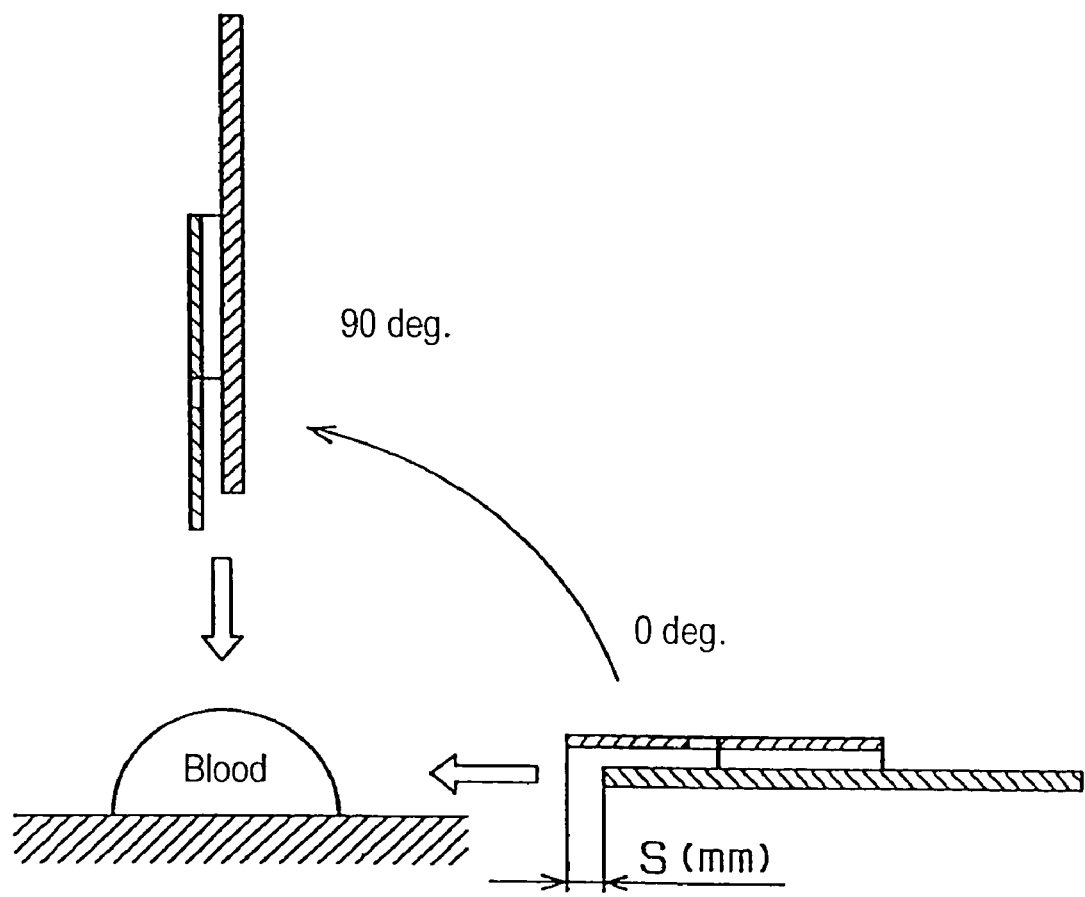
FIG. 21 illustrates a test method of sucking blood by the biosensor.

Surface active agent is applied to the surface of the cover (inside of the sample supplying path) in order to supply the blood to the path more quickly. FIG. 21 illustrates a test method for confirming a blood-sucking performance of the sensor depending on a blood-supplying angle in the blood-sugar value sensor discussed above. Table 1 shows the test result.

TABLE 1

|  | S (mm) | Blood Supply Angle (deg.) | 1 | 2 | 3 | 4 | 5 |
|---|---|---|---|---|---|---|---|
| Conventional Sensor | 0 | 0 | x | x | x | x | x |
|  |  | 15 | Δ | x | x | Δ | x |
|  |  | 30 | Δ | Δ | Δ | x | Δ |
|  |  | 45 | o | o | o | o | Δ |
|  |  | 90 | o | o | o | o | o |
| Sensor According to Present Invention | 0.1 | 0 | o | Δ | Δ | o | Δ |
|  |  | 15 | o | Δ | o | o | Δ |
|  |  | 30 | o | o | o | o | Δ |
|  |  | 45 | o | o | o | o | o |
|  |  | 90 | o | o | o | o | o |
|  | 0.25 | 0 | o | o | o | o | o |
|  |  | 15 | o | o | o | o | o |
|  |  | 30 | o | o | o | o | o |
|  |  | 45 | o | o | o | o | o |
|  |  | 90 | o | o | o | o | o |
|  | 0.5 | 0 | o | o | o | o | o |
|  |  | 15 | o | o | o | o | o |
|  |  | 30 | o | o | o | o | o |
|  |  | 45 | o | o | o | o | o |
|  |  | 90 | o | o | o | o | o |
|  | 1.0 | 0 | o | o | o | o | o |
|  |  | 15 | o | o | o | o | o |
|  |  | 30 | o | o | o | o | o |
|  |  | 45 | o | o | o | o | o |
|  |  | 90 | o | o | o | o | o |
|  | 2.0 | 0 | o | o | o | o | o |
|  |  | 15 | o | o | o | o | o |
|  |  | 30 | o | o | o | o | o |
|  |  | 45 | o | o | o | o | o |
|  |  | 90 | o | o | o | o | o |

Definitions of the marks in the table:
o: The blood is sucked by one sucking.
Δ: The blood is sucked by two or three sucking operations.
x: The blood is not sucked at all.

Table 1 tells that the conventional sensor having distance S=0 mm does not suck blood and requires several trials of supply for proper sucking when it has a small blood-supplying angle (0-30 degree). For a small blood-supplying angle, when a user supplies the blood to the sample supplying path, the blood attaches to the rear side of the insulating board firstly. Thus even if the user tries to supply the blood again, the blood is pulled by the blood attached to the rear side. This may be a reason why the conventional sensor does not work well.

The sensor of the present invention, on the other hand, sometimes requires several sucking operations when the blood-supplying angle is small even at the shortest distance S=0.1 mm; however the sensor does suck the blood at all. When the distance S is not less than 0.25 mm, the sensor sucks the blood easily at any sucking angle.

Figure 22:
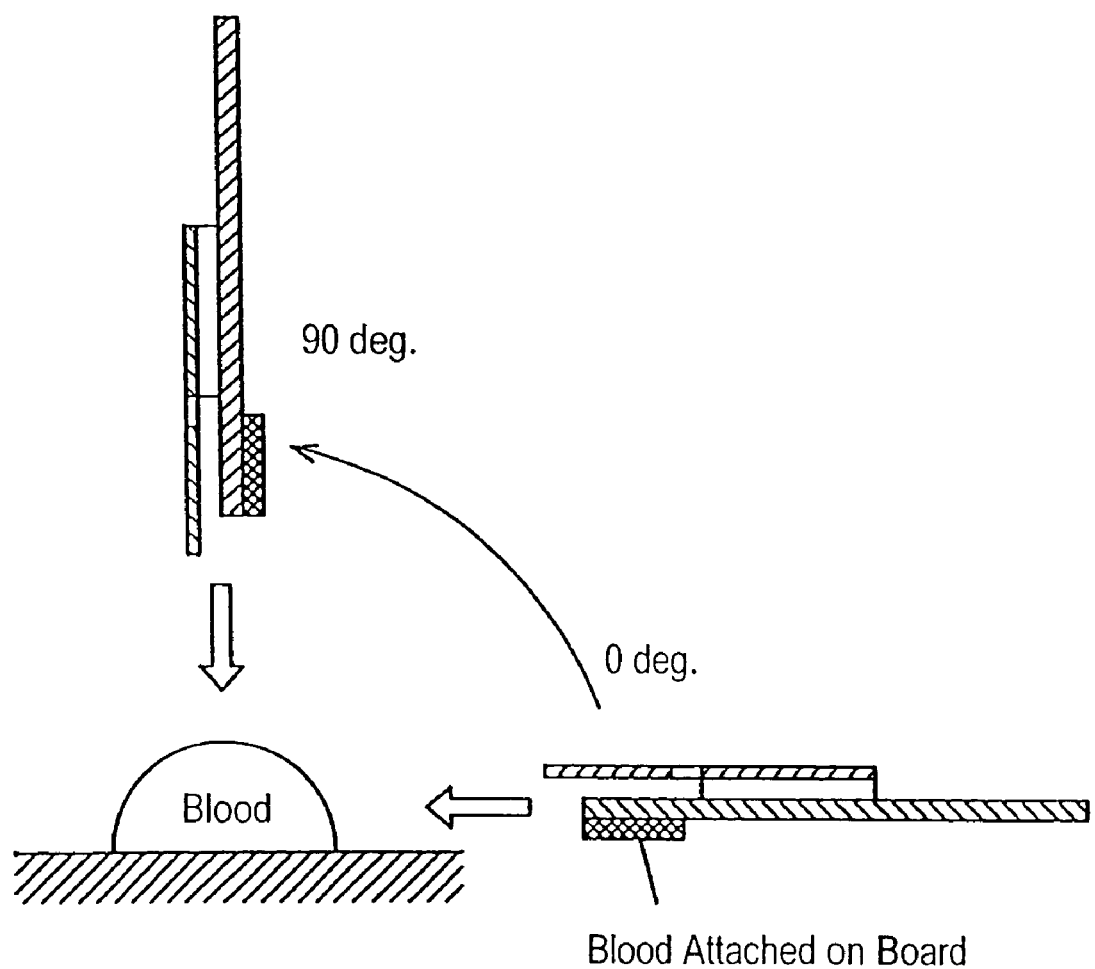
FIG. 22 illustrates another test method of sucking blood by the biosensor.

FIG. 22 illustrates a test method for testing the sensor in the blood-sucking performance depending on the blood-supplying angle. In this test, blood is attached to the rear side of the insulating board in advance at an area of 5 mm from the end of the board in order to prevent the blood from being sucked. Table 2 shows the test result.

TABLE 2

| | S (mm) | Blood Supply Angle (deg.) | 1 | 2 | 3 | 4 | 5 |
|---|---|---|---|---|---|---|---|
| Conventional Sensor | 0 | 0 | x | x | x | x | x |
| | | 15 | x | x | x | x | x |
| | | 30 | x | x | x | x | x |
| | | 45 | x | x | x | x | x |
| | | 90 | x | x | x | x | x |
| Sensor According to Present Invention | 0.1 | 0 | x | Δ | Δ | Δ | x |
| | | 15 | Δ | Δ | Δ | x | Δ |
| | | 30 | Δ | o | Δ | o | Δ |
| | | 45 | o | o | o | o | o |
| | | 90 | o | o | o | o | o |
| | 0.25 | 0 | o | o | o | o | o |
| | | 15 | o | o | o | o | o |
| | | 30 | o | o | o | o | o |
| | | 45 | o | o | o | o | o |
| | | 90 | o | o | o | o | o |
| | 0.5 | 0 | o | o | o | o | o |
| | | 15 | o | o | o | o | o |
| | | 30 | o | o | o | o | o |
| | | 45 | o | o | o | o | o |
| | | 90 | o | o | o | o | o |
| | 1.0 | 0 | o | o | o | o | o |
| | | 15 | o | o | o | o | o |
| | | 30 | o | o | o | o | o |
| | | 45 | o | o | o | o | o |
| | | 90 | o | o | o | o | o |
| | 2.0 | 0 | o | o | o | o | o |
| | | 15 | o | o | o | o | o |
| | | 30 | o | o | o | o | o |
| | | 45 | o | o | o | o | o |
| | | 90 | o | o | o | o | o |

Definitions of the marks in the table:
o: The blood is sucked by one sucking.
Δ: The blood is sucked by two or three sucking operations.
x: The blood is not sucked at all.

Table 2 shows that the conventional sensor having the distance S=0 mm can not suck the blood except the blood-supplying angle of 90 degree. On the other hand, the sensor of the present invention sometimes cannot suck the blood when distance S=0.1 mm at a small blood-supplying angle. However, the sensor can suck the blood easily at any blood-supplying angle when distance S is not less than 0.25 mm.

According to the second embodiment discussed above, the respective ends of first insulating board 51 and second insulating board 58 are deviated each other so that both the ends are placed at different places viewed from a plan view. This allows the sample liquid to be sucked exactly and easily.

In the second embodiment, an enzyme sensor as the biosensor is described. The present invention is similarly applicable to biosensors including a molecular recognition element reacting not only with the enzyme but also with germ, antibody, DNA, or RNA.

According to the sensor in accordance with the second embodiment, two boards bonded together form the sample supplying path, from which the sample liquid is taken out, between the boards. An opening is provided as an inlet at respective ends of both boards for accepting the sample liquid. The ends forming the inlet are located at different places or shaped in different forms viewed from a plan view of the biosensor. Thus the supply sample liquid can be sucked exactly and easily even if the sample-supplying angle is not enough (small). Further this prevents the sample liquid from attaching to the rear side of first insulating board 51. If the sample liquid attaches to the rear side, a user can supply the sample liquid again to allowing the sample liquid to be supplied smoothly.

INDUSTRIAL APPLICABILITY

The present invention provides a biosensor which is handled by a user easily and exhibits an excellent measurement accuracy. The present invention also provides a measuring method using the biosensor as well as a measuring device using the biosensor.

The invention claimed is:
1. A method of measuring a quantity of a substrate included in a sample liquid, comprising the steps of:
   providing a biosensor which includes:
      an insulating board;
      an electrode section formed on at least a part of the insulating board, the electrode section including a counter electrode, a measuring electrode, and a detecting electrode:
      a sample supplying path for supplying the sample liquid to the electrode section; and
      a reagent layer for reacting with the sample liquid supplied through the sample supplying path, wherein the detecting electrode is disposed most downstream among the counter electrode, the measuring electrode, and the detecting electrode along the sample supplying path from an inlet along a direction of flow of the sample liquid;
   providing a measuring device which includes:
      a supporting section for detachably supporting the biosensor; and
      a connecting terminal and a driving power supply for applying a voltage to the electrode section;
   inserting the biosensor into the supporting section of the measuring device;
   applying a voltage with the driving power supply to a first group including the counter electrode and the measuring electrode; and
   applying a voltage with the driving power supply to a second group including the detecting electrode and one of the measuring electrode and the counter electrode; and
   determining whether or not the sample liquid is supplied sufficiently for measurement depending on whether or not respective electric currents supplied from the first and second groups exceed respective predetermined thresholds.

2. The method of claim 1, wherein said step of determining whether or not the sample liquid is supplied sufficiently comprises the sub-step of:
   determining that the sample liquid is insufficient when the electric current from the second group does not exceed the predetermined threshold within a given lapse of time since the electric current from the first group exceeds the predetermined threshold.

3. The method of claim 2, further comprising the step of:
   when it is determined that the sample liquid is insufficient, outputting the determination to outside of the measuring device.

4. The method of claim 1, further comprising the step of:
   halting steps of measuring in order to add the sample liquid when the electric current from the second group does not exceed the predetermined threshold within a given lapse of time since the electric current from the first group exceeds the predetermined threshold.

5. The method of claim 1, wherein an air hole is provided more downstream than the detecting electrode for accelerating the flow of the sample liquid, said method further comprising the step of:

determining that the sample liquid is sucked from the air hole by mistake when the electric current from the second group exceeds the predetermined threshold before the electric current from the first group exceeds the predetermined threshold and when the electric current from the first group does not exceed the predetermined threshold within a given lapse of time.

6. The method of claim 1, further comprising the step of:

compensating a measured quantity of the substrate corresponding to an electric current detected at the electrode section depending on a lapse of time since the electric current from the first group exceeds the predetermined threshold until the electric current from the second group exceeds the predetermined threshold.

7. The method of claim 6, wherein the measuring device further includes a memory for storing calibration data indicating correspondence between an electric current detected at the biosensor and a quantity of the substrate in the sample liquid, said method further comprising the step of:

determining a quantity of the substrate corresponding to the detected electric current referring to the calibration data stored in the memory.

8. The method of claim 1, further comprising the step of:

incubating reaction between the sample liquid and the reagent layer after the sample liquid is supplied to the sample supplying path; and varying a time for said step of incubating the reaction according to a lapse of time since the electric current from the first group exceeds the predetermined threshold until the electric current from the second group exceeds the predetermined threshold.

9. The method of claim 1, further comprising:

switching the voltage applied to one of the first and second groups at a given interval.

* * * * *

UNITED STATES PATENT AND TRADEMARK OFFICE
Certificate

Patent No. 7,850,839 B2            Patented: December 14, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Shoji Miyazaki, Matsuyama (JP); Hiroyuki Tokunaga, Onsen-gung (JP); and Yoshinobu Tokuno, Iyo-gun (JP).

Signed and Sealed this Twentieth Day of September 2011.

<div style="text-align:right">

KEITH D. HENDRICKS
*Supervisory Patent Examiner*
Art Unit 1724
Technology Center 1700

</div>